United States Patent [19]

Cunningham, Jr. et al.

[11] Patent Number: 5,744,341
[45] Date of Patent: Apr. 28, 1998

[54] GENES OF CAROTENOID BIOSYNTHESIS AND METABOLISM AND A SYSTEM FOR SCREENING FOR SUCH GENES

[75] Inventors: Francis X. Cunningham, Jr., Chevy Chase; Zairen Sun, Hyattsville, both of Md.

[73] Assignee: University of Maryland College Park, College Park, Md.

[21] Appl. No.: 624,125

[22] Filed: Mar. 29, 1996

[51] Int. Cl.[6] .............................. C12N 1/21; C12N 9/02; C12N 15/53; C12N 15/63
[52] U.S. Cl. .................. 435/189; 435/252.3; 435/254.11; 435/320.1; 435/325; 536/23.2
[58] Field of Search .............................. 435/189, 320.1, 435/325, 252.3, 254.11, 419; 536/23.2

[56] References Cited

U.S. PATENT DOCUMENTS 5,539,093  7/1996  Fitzmaurice et al. ................ 536/23.2
5,589,581 12/1996  Misawa et al. ...................... 536/23.2

OTHER PUBLICATIONS

Buckner et al., Meth. Enzymol. 214:311–323, 1993.
Goodwin, Meth. Enzymol. 214:331–340, 1993.
Archives of Biochemistry and Biophysics, vol. 230, No. 2, pp. 446–454, 1984, Sandra L. Spurgeon, et al., "Isopentenyl Pyrophosphate Isomerase and Prenyltransferase From Tomato Fruit Plastids".

FEBS Letters, vol. 328, No. 1–2, pp. 130–138, Aug. 1993, Francis X. Cunningham, Jr., et al., "Cloning and Functional Expression in *Escherichia coli* of a Cyanobacterial Gene for Lycopene Cyclase, The Enzyme That Catalyzes the Biosynthesis of β–Carotene".

The Journal of Biological Chemistry, vol. 271, No. 13, Mar. 29, 1996, pp. 7774–7780, Núria Cunillera, et al., "*Arabidopsis thaliana* Contains Two Differentially Expressed Farnesyl–Diphosphate Synthase Genes".

The Journal of Biological Chemistry, vol. 271, No. 40, pp. 24349–24352, Oct. 4, 1996, Zairen Sun, et al., "Cloning and Functional Analysis of the β–Carotene Hydroxylase of *Arabidopsis thaliana*".

Annual Review of Plant Physiology and Molecular Biology, vol. 45, pp. 287–301, Glenn E. Bartley, et al., "Molecular Biology of Carotenoid Biosynthesis in Plants" (1994).

*Primary Examiner*—Eric Grimes
*Attorney, Agent, or Firm*—Oblon, Spivak, McClelland, Maier & Neustadt, P.C.

[57] ABSTRACT

The present invention also describes the DNA sequence for eukaryotic genes encoding ε cyclase, isopentenyl pyrophosphate isomerase and β-carotene hydroxylase as well as vectors containing the same and hosts transformed with said vectors. The present invention provides methods for controlling the ratio of various carotenoids in a host and for the production of novel carotenoid pigments. The present invention also provides a method for screening for eukaryotic genes encoding carotenoid biosynthesis.

7 Claims, 24 Drawing Sheets

FIG. 4A
ARABIDOPSIS THALIANA EPSILON CYCLASE:

```
     acaaaaggaaataattag attcctctttctgcttgctataccttgata         48 gaacaatataacaatggtgtaagtcttctc gctgtattcgaaattatttggaggaggaaa  108 atggagtgtgttggggctaggaatttcgca gcaatggcggtttcaacatttccgtcatgg  168
  1  M  E  C  V  G  A  R  N  F  A   A  M  A  V  S  T  F  P  S  W agttgtcgaaggaaatttccagtggttaag gagtacagctataggaatattcgtttcggt  228
 21  S  C  R  R  K  F  P  V  V  K   R  Y  S  Y  R  N  I  R  F  G ttgtgtagtgtcagagctagcggcggcgga agttccggtagtgagagttgtgtagcggtg  288
 41  L  C  S  V  R  A  S  G  G  G   S  S  G  S  E  S  C  V  A  V agagaagatttcgctgacgaagaagatttt gtgaaagctggtggttctgagattctattt  348
 61  R  E  D  F  A  D  E  E  D  F   V  K  A  G  G  S  E  I  L  F gttcaaatgcagcagaacaaagatatggat gaacagtctaagcttgttgataagttgcct  408
 81  V  Q  M  Q  Q  N  K  D  M  D   E  Q  S  K  L  V  D  K  L  P cctatatcaattggtgatggtgctttggat catgtggttattggttgtggtcctgctggt  468
101  P  I  S  I  G  D  G  A  L  D   H  V  V  I  G  C  G  P  A  G ttagccttggctgcagaatcagctaagctt ggattaaaagttggactcattggtccagat  528
121  L  A  L  A  A  E  S  A  K  L   G  L  K  V  G  L  I  G  P  D cttcctttttactaacaattacggtgtttgg gaagatgaattcaatgatcttgggctgcaa  588
141  L  P  F  T  N  N  Y  G  V  W   E  D  E  F  N  D  L  G  L  Q aaatgtattgagcatgtttggagagagact attgtgtatctggatgatgacaagcctatt  648
161  K  C  I  E  H  V  W  R  E  T   I  V  Y  L  D  D  D  K  P  I accattggccgtgcttatggaagagttagt cgacgtttgctccatgaggagcttttgagg  708
181  T  I  G  R  A  Y  G  R  V  S   R  R  L  L  H  E  E  L  L  R aggtgtgtcgagtcaggtgtctcgtacctt agctcgaaagttgacagcataacagaagct  768
201  R  C  V  E  S  G  V  S  Y  L   S  S  K  V  D  S  I  T  E  A
```

FIG. 4B

```
        tctgatggccttagacttgttgcttgtgac gacaataacgtcattccctgcaggcttgcc  828
221     S  D  G  L  R  L  V  A  C  D   D  N  N  V  I  P  C  R  L  A actgttgcttctggagcagcttcgggaaag ctcttgcaatacgaagttggtggacctaga  888
241     T  V  A  S  G  A  A  S  G  K   L  L  Q  Y  E  V  G  G  P  R gtctgtgtgcaaactgcatacggcgtggag gttgaggtggaaaatagtccatatgatcca  948
261     V  C  V  Q  T  A  Y  G  V  E   V  E  V  E  N  S  P  Y  D  P gatcaaatggttttcatggattacagagat tatactaacgagaaagttcggagcttagaa 1008
281     D  Q  M  V  F  M  D  Y  R  D   Y  T  N  E  K  V  R  S  L  E gctgagtatccaacgtttctgtacgccatg cctatgacaaagtcaagactcttcttcgag 1068
301     A  E  Y  P  T  F  L  Y  A  M   P  M  T  K  S  R  L  F  F  E gagacatgtttggcctcaaaagatgtcatg ccctttgatttgctaaaaacgaagctcatg 1128
321     E  T  C  L  A  S  K  D  V  M   P  F  D  L  L  K  T  K  L  M ttaagattagatacactcggaattcgaatt ctaaagacttacgaagaggagtggtcctat 1188
341     L  R  L  D  T  L  G  I  R  I   L  K  T  Y  E  E  E  W  S  Y atcccagttggtggttccttgccaaacacc gaacaaaagaatctcgcctttggtgctgcc 1248
361     I  P  V  G  G  S  L  P  N  T   E  Q  K  N  L  A  F  G  A  A gctagcatggtacatcccgcaacaggctat tcagttgtgagatctttgtctgaagctcca 1308
381     A  S  M  V  H  P  A  T  G  Y   S  V  V  R  S  L  S  E  A  P aaatatgcatcagtcatcgcagagatacta agagaagagactaccaaacagatcaacagt 1368
401     K  Y  A  S  V  I  A  E  I  L   R  E  E  T  T  K  Q  I  N  S aatatttcaagacaagcttgggatacttta tggccaccagaaaggaaaagacagagagca 1428
421     N  I  S  R  Q  A  W  D  T  L   W  P  P  E  R  K  R  Q  R  A
```

FIG. 4C

```
     ttctttctcttggtcttgcactcatagtt caattcgatacctgaaggcattagaagcttc  1488
     F F F F G L A L I V   Q F D T E G I R S F
441 ttccgtactttcttccgccttcaaaatgg atgtggcaagggtttctaggatcaacatta    1548
     F R T F F R L P K W   M W Q G F L G S T L
461 acatcaggagatctcgtttctctttgctttta tacatgttcgtcatttcaccaacaatttg  1608
     T S G D L V L F A L   Y M F V I S P N N L
481 agaaaaggtctcatcaatcatctcatctct gatcaaccggagcaaccatgataaaaaacc  1668
     R K G L I N H L I S   D P T G A T M I K T
501 tatctcaaagtatgatttacttatcaactc ttaggtttgtgtatatatatgttgatttat  1728
     Y L K V
521 ctgaataatcgatcaaagaatggtatgtgg gttactaggaagttggaaacaaacatgtat  1788 agaattcaagggagtgatcgaaatggagatg gaaacgaaaagaaaaaatcagtctttgtt  1848
                                                                   1660
     ttgtggttagtg
```

FIG. 5A

```
  1  gctctttctc ctcctcctct accgattccc gactccgcct cccgaaatcc
 51  ttatccggat tctctccgtc tcttcgattt aacgcttttt ctgtctgtta
101  cgtcgtcgaa gaacggagac agaattctcc gattgagaac gatgagagac
151  cggagagcac gagctccaca aacgctatag acgctgagta tctggcgttg
201  cgtttggcgg agaaattgga gaggaagaaa tcggagaggt ccacttatct
251  aatcgctgct atgtgtcga gcttggtat cacttctatg gctgttatgg
301  ctgtttacta cagattctct tgctctctct gttggtgctg ctgttggtat
351  ttgaaatgt ttggtacatt tgctctctct gttggtgctg gcttctctat
401  ggaattctgg gcaagatggg ctcatagagc tctgtggcac tctgtggcac gctccctctc
451  ggaatatgca tgagtcacat cacaaaccaa gagaaggacc gtttgagcta
501  aacgatgttt ttgctatagt gaacgctggt ccagcgattg gtctcctctc
551  ttatggattc ttcaataaag gactcgttcc tggtctctgc tttggcgcg
601  ggttaggcat aacggtgttt ggaatcgcct acatgtttgt ccacgatggt
651  ctcgtgcaca agcgtttccc tgtaggtccc atcgccgacg tcccttacct
```

FIG. 5B

```
701  ccgaaaggtc gccgccgctc accagctaca tcacacagac aagttcaatg
751  gtgtaccata tggactgttt cttggaccca aggaattgga agaagttgga
801  ggaaatgaag agttagataa ggagattagt cggagaatca atcatacaa
851  aaaggcctcg ggctccgggt cgagttcgag ttcttgactt taaacaagtt
901  ttaaatccca aattctttt ttgtctttctg tcattatgat catctttaaga
951  cggtct
```

FIG. 6

```
                                                                                                                    64
A. thal.          SFSS SSTDFRLRLP KSLSGFSPSL RFKRFSVCYV VEERRQNSPI ENDERPESTS STNAIDAEYL
                                                                                                                   144
A. thal.    ALRLAEKLER KKSERSTYLI AAMLSSFGIT SMAVMAVYYR FSWQMEGGEI SMLEMFGTFA LSVGAAVGME FWARWAHRAL
Ali cal.    ..........  ..........  ..........  ..........  ..........  ..........  MTQFL IVVATVLVME LTAYSVHRWI
A. aurant.  ..........  ..........  ..........  ..........  ..........  ..........  MTNFL IVVATVLVME LTAYSVHRWI
E. herb.    ..........  ..........  ..........  ..........  ..........  ..........  ML.NSL IVILSVIAME GIAAFTHRYI
E. ured.    ..........  ..........  ..........  ..........  ..........  ..........  MLWIWNAL IVFVTVIGME VIAALAHKYI
consensus   ---------- ---------- ---------- ---------- ---------- ----f----- ---v---ME --A---Hr--

PREDICTED TM HELIX                                      224
A. thal.    WHASL.WNMH ESHHKPREGP FELNDVFAIV NAGPAIGLLS YGFFNKGLVP GLCFGAGLGI TVFGIAYMFV HDGLVHKRFP
Ali cal.    MHGPLGWGWH KSHEEHDHA  LEKNDLYGVV FAVLATILFT VGAYWWPVLW VI.....ALGM TVYGLIYFIL HDGLVHQRWP
A. aurant.  MHGPLGWGWH KSHEEHDHA  LEKNDLYGLV FAVIATVLFT VGWIWAPVLW VI.....ALGM TVYGLIYFVL HDGLVHQRWP
E. herb.    MHG.WGNRWH ESHHTPRKGV FELNDLFAVV FAGVAIALIA VGTAGVWPLQ VI.....GCGM TVYGLLYFLV HDGLVHQRWP
E. ured.    MHG.WGWGWH LSHHEPRKGA FEVNDLYAVV FAALSILLIY LGSTGMWPLQ VI.....GAGM TAYGLLYFMV HDGLVHQRWP
consensus   -H--l-W-H  -SHH-pr-g- fE-ND-a-V  -A--ai--L--  -G-------- ------glG- Tv-G--Y--v HDGLVH-R-P PREDICTED TM HELIX                                             301
A. thal.    VGPIADVPYL RKVAAAHQLH HT..DKFNGV PYGLFLGPKE LEEVGGNEEL DKEISRRIKS YKKASGSGS SSSS*......
Ali cal.    FRYIPRRGYF RRLYQAHRLH HAVEGRDHCV SFGFIYAPP. VDKLKQDLKR SGVLRPQDER PS*.........
A. aurant.  FRYIPRKGYA RRLYQAHRLH HAVEGRDHCV SFGFIYAPP. VDKLKQDLKM SGVLRAEAQE RT*.........
E. herb.    FHWIPRRGYL KRLYVAHRLH HAVRGREGCV SFGFIYARK. PADLQAILRE RHGRPPKRDA AKDRPDAASP SSSSPE*
E. ured.    FRYIPRKGYL KRLYMAHRMH HAVRGKEGCV SFGFLYAPP. LSKLQATLRE RHG..ARAGA ARDAQGGEDE PASGK*.
consensus   ---I----Y-- r-----AH-H H-------V  ---------- -----G----  -------p--  ---------- ----S-----
```

FIG. 7A

```
  1  ccacgggtcc gcctccccgt ttttttccga tccgatctcc ggtgccgagg
 51  actcagctgt ttgttcgcgc tttctcagcc gtcaccatga ccgattctaa
101  cgatgctgga atggatgctg ttcagagacg actcatgttt gaagacgaat
151  gcattctcgt tgatgaaaat aatcgtgtgg tgggacatga cactaagtat
201  aactgtcatc tgatggaaaa gattgaagct gagaatttac ttcacagagc
251  tttcagtgtg tttttattca actccaagta tgagttgctt ctccagcaac
301  ggtcaaaaac aaaggttact ttcccacttg tgtggacaaa cacttgttgc
351  agccatcctc tttaccgtga atccgagctt attgaagaga atgtgcttgg
401  tgtaagaaat gccgcacaaa ggaagctttt cgatgagctc ggtattgtag
451  cagaagatgt accagtcgat gagttcactc ccttgggacg catgctttac
```

FIG. 7B

```
501  aaggcacctt ctgatgggaa atggggagag cacgaagttg actatctact
551  cttcatcgtg cgggatgtga agcttcaacc aaacccagat gaagtggctg
601  agatcaagta cgtgagcagg gaagagctta aggagctggt gaagaaagca
651  gatgctggcg atgaagctgt gaaactatct ccatggttca gattggtggt
701  ggataatttc ttgatgaagt ggtgggatca tgttgagaaa ggaactatca
751  ctgaagctgc agacatgaaa accattcaca agctctgaac tttccataag
801  ttttggatct tccccttccc ataataaaat taagagatga gactttatt
851  gattacagac aaaactggca acaaaatcta ttcctaggat ttttttttgc
901  ttttatttta cttttgattc atctctagtt tagtttcat cttaaaaaa
951  aaaa
```

FIG. 8A

```
  1  caccaatgtc tgtttcttct ttatttaatc tcccattgat tcgcctcaga
 51  tctctcgctc tttcgtcttc ttttctttct ttccGATTTG CCCATCGTCC
101  TCTGTCATCG ATTTCACCGA GAAAGTTACC GAATTTTCGT GCTTTCTCTG
151  GTACCGCTAT GACAGATACT AAAGATGCTG GTATGGATGC TGTTCAGAGA
201  CGTCTCATGT TTGAGGATGA ATGCATTCTT GTTGATGAAA CTGATCGTGT
251  TGTGGGGCAT GTCAGCAAGT ATAATTGTCA TCTGATGGAA AATATTGAAG
301  CCAAGAATTT GCTGCACAGG GCTTTTAGTG TATTTTTATT CAACTCGAAG
351  TATGAGTTGC TTCTCCAGCA AAGGTCAAAC ACAAAGGTTA CGTTCCCTCT
401  AGTGTGGACT AACACTTGTT GCAGCCATCC TCTTTACCGT GAATCAGAGC
451  TTATCCAGGA CAATGCACTA GGTGTGAGGA ATGCTGCACA AAGAAAGCTT
```

FIG. 8B

```
501  CTCGATGAGC TTGGTATTGT AGCTGAAGAT GTACCAGTCG ATGAGTTCAC
551  TCCCTTGGGA CGTATGCTGT ACAAGGCTCC TTCTGATGGC AAATGGGGAG
601  AGCATGAACT TGATTACTTG CTCTTCATCG TGCGAGACGT GAAGGTTCAA
651  CCAAACCCAG ATGAAGTAGC TATGTGAGCC GGGAAGAGCT
701  GAAGGAGCTG GTGAAGAAAG CAGATGCAGG TGAGGAAGGT TTGAAACTGT
751  CACCATGGTT CAGATTGGTG GTGGACAATT TCTTGATGAA GTGGTGGGAT
801  CATGTTGAGA AAGGAACTTT GGTTGAAGCT ATAGACATGA AAACCATCCA
851  CAAACTCTGA ACATCTTTTT TTAAAGTTTT TAAATCAATC AACTTTCTCT
901  TCATCATTTT TATCTTTTCG ATGATAATAA TTTGGGATAT GTGAGACACT
951  TACAAAACTT CCAAGCACCT CAGGCAATAA TAAAGTTTGC GGCCGC
```

FIG. 9A

```
  1  CTCGGTAGCT GGCCACAATC GCTATTTGGA ACCTGGCCCG GCGGCAGTCC
 51  GATGCCGCGA TGCTTCGTTC GTTGCTCAGA GGCCTCACGC ATATCCCCCG
101  CGTGAACTCC GCCCAGCAGC CCAGCTGTGC ACACGGCGA CTCCAGTTTA
151  AGCTCAGGAG CATGCAGATG ACGCTCATGC AGCCCAGCAT CTCAGCCAAT
201  CTGTCGCGCG CCGAGGACCG CACAGACCAC ATGAGGGGTG CAAGCACCTG
251  GGCAGGGCGG CAGTCGCCAGG ATGAGCTGAT GCTGAAGGAC GAGTGCATCT
301  TGGTGGATGT TGAGACAAC ATCACAGGCC ATGCCAGCAA GCTGGAGTGT
351  CACAAGTTCC TACCACATCA GCCTGCAGGC CTGCTGCACC GGGCCTTCTC
401  TGTGTTCCTG TTTGACGATC AGGGGCGACT GCTGCTGCAA CAGCCGTGCAC
451  GCTCAAAAAT CACCTTCCCA AGTGTGTGGA CGAACACCTG CTGCAGCCAC
501  CCTTTACATG GGCAGACCCC AGATGAGGTG GACCAACTAA GCCAGGTGGC
551  CGACGGAACA GTACCTGGCG CAAAGGCTGC TGCCATCCGC AAGTTGGAGC
```

FIG. 9B

```
601   ACGAGCTGGG GATACCAGCG CACCAGCTGC CGGCAAGCGC GTTTCGCTTC
651   CTCACGCGTT TGCACTACTG TGCCCGCGGAC GTGCAGCCAG CTGCGACACA
701   ATCAGCGCTC TGGGGCGAGC ACGAAATGGA CTACATCTTG TTCATCCGGG
751   CCAACGTCAC CTTGGCGCCC AACCCTGACG AGGTGGACGA AGTCAGGTAC
801   GTGACGCAAG AGGAGCTGCG GCAGATGATG CAGCCCGGACA ACGGGCTGCA
851   ATGGTCGCCG TGGTTTCGCA TCATCGCCCGC GCGCTTCCTT GAGCGTTGGT
901   GGGCTGACCT GGACGCGGCC CTAAACACTG ACAAACACGA GGATTGGGGA
951   ACGGTGCATC ACATCAACGA AGCGTGAAAG CAGAAGCTGC AGGATGTGAA
1001  GACACGTCAT GGGGTGGAAT TGCCGTACTTG GCAGCTTCGT ATCTCCTTTT
1051  TCTGAGACTG AACCTGCAGT CAGGTCCCAC AAGGTCAGGT AAAATGGCTC
1101  GATAAAATGT ACCGTCACTT TTTGTCGCCGT ATACTGAACT CCAAGAGGTC
1151  AAAAAAAAAA AAAA
```

FIG. 10A

```
  1  CTCGGTAGCT GGCCACAATC GCTATTTGGA ACCTGGCCCG GCGGCAGTCC
 51  GATGCCGCGA TGCTTCGTTC GTTGCTCAGA GGCCTCACGC ATATCCCGCG
101  CGTGAACTCC GCCCAGCAGC CCAGCTGTGC ACACGCGCGA CTCCAGTTTA
151  AGCTCAGGAG CATGCAGCTG CTTTCCGAGG ACCGCACAGA CCACATGAGG
201  GGTGCAAGCA CCTGGGCAGG CGGGCAGTCG CAGGATGAGC TGATGCTGAA
251  GGACGAGTGC ATCTTGGTAG ATGTTGAGGA CAACATCACA GGCCATGCCA
301  GCAAGCTGGA GTGTCACAAG TTCCTACCAC ATCAGCCTGC AGGCCTGCTG
351  CACCGGGCCT TCTCTGTGTT CCTGTTTGAC GATCAGGGGC GACTGCTGCT
401  GCAACAGCGT GCACGCTCAA AAATCACCTT CCCAAGTGTG TGGACGAACA
451  CCTGCTGCAG CCACCCTTTA CATGGGCAGA CCCCAGATGA GGTGGACCAA
501  CTAAGCCAGG TGGCCGACGG AACAGTACCT GGGCAAAGG CTGCTGCCAT
551  CCGCAAGTTG GAGCACGAGC TGGGATACC AGCGCACCAG CTGCCGGCAA
601  GGCGTTTCG CTTCCTCACG CGTTTGCACT ACTGTGCCGC GGACGTGCAG
```

FIG. 10B

```
 651  CCAGCTGCGA CACAATCAGC GCTCTGGGGC GAGCACGAAA TGGACTACAT
 701  CTTGTTCATC CGGGCCAACG TCACCTTGGC GCCCAACCCT GACGAGGTGG
 751  ACGAAGTCAG GTACGTGACG CAAGAGGAGC TGCGGCAGAT GATGCAGCCG
 801  GACAACGGGC TTCAATGGTC GCCGTGGTTT CGCATCATCG CCGCGCGCTT
 851  CCTTGAGCGT TGGTGGGCTG ACCTGGACGC GGCCCTAAAC ACTGACAAAC
 901  ACGAGGATTG GGGAACGGTG CATCACATCA ACGAAGCGTG AAGGCAGAAG
 951  CTGCAGGATG TGAAGACACG TCATGGGGTG GAATTGCGTA CTTGGCAGCT
1001  TCGTATCTCC TTTTCTGAG ACTGAACCTG CAGAGCTAGA GTCAATGGTG
1051  CATCATATTC ATCGTCTCTC TTTGTTTTA GACTAATCTG TAGCTAGAGT
1101  CACTGATGAA TCCTTTACAA CTTTCAAAAA AAAAA
```

```
                                                              50
        1
HP04    MLRSLLRGLT HIPRVNSAQQ PSCAHARLQF KLRSMQMTLM QPSISANLSR
HP05    MLRSLLRGLT HIPRVNSAQQ PSCAHARLQF KLRSMQLL.. ..........
ATDP7   MSVSSLFNLP .LIRLRSLA. AHRPLSSIS. .......... PRKLPNFRAF
C brew. MS.SSMLNFT .ASRIVSLPL LSSPFSSFRF PLCFFSPISL TQRFSAKLTF
ATDP5   .......... .TGPPPRFFP IRSPVPRTQL FVRAFSAV.. ..........
S cerev. ..MTADNNSM PHGAVSSYAK LVQNQTPEDI LEEFPEIIPL QQRPN...TR 100
        51
HP04    AEDRTDHMRG ASTWAGGQSQ DELMLKDECI LVDVEDNITG HASKLECHKF
HP05    SEDRTDHMRG ASTWAGGQSQ DELMLKDECI LVDVEDNITG HASKLECHKF
ATDP7   S..GTA.MTD TKDAGMDAVQ RRLMFEDECI LVDETDRVVG HVSKYNCHLM
C brew. SSQATT.MGE VVDAGMDAVQ RRLMFEDECI LVDEMDKVVG HESKYNCHLM
ATDP5   ....T.MTD  SNDAGMDAVQ RRLMFEDECI LVDEMNRVVG HDTKYNCHLM
S cerev. SSETSNDESG ETCFSGHDEE QIKLMNENCI VLDWDDNAIG AGTKKVCHLM 150
        101
HP04    LPHQPAGLLH RAFSVFLFDD QGRLLLQQRA RSKITFPSVW TNTCCSHPLH
HP05    LPHQPAGLLH RAFSVFLFDD QGRLLLQQRA RSKITFPSVW TNTCCSHPLH
ATDP7   ENIEAKNLLH RAFSVFLFNS QGRLLLQQRS NTKVTFPLVW TNTCCSHPLY
C brew. EKIESENLLH RAFSVFLFNS KYELLLQQRS ATKVTFPLVW TNTCCSHPLY
ATDP5   EKIEAENLLH RAFSVFLFNS KYELLLQQRS KTKVTFPLVW TNTCCSHPLY
S cerev. ENIE.KGLLH RAFSVFIFNE QGELLLQQRA TEKITFPDLM TNTCCSHPLC 200
        151
HP04    GQTPDEVDQL SQVADGTVPG AKAAAIRKLE HELGIPAHQL PA..SAFRFLT
HP05    GQTPDEVDQL SQVADGTVPG AKAAAIRKLE HELGIPAHQL PA..SAFRFLT
ATDP7   RE........ SELIQDNALG VRNAAQRKLL DELGIVAEDV PV.DEFTPLG
C brew. RE........ SELIDENCLG VRNAAQRKLL DELGIPAEDL PV.DQFIPLS
ATDP5   RE........ SELIEENVLG VRNAAQRKLF DELGIVAEDV PV.DEFTPLG
S cerev. ID...DELGL KGKLDDKIKG AITAAVRKLD HELGIPEDET KTRGKFHFLN
```

```
201
RLHYCAADVQ PAATQSALWG EHEMDYILFI .....RANVTL APNPDEVDEV
RLHYCAADVQ PAATQSALWG EHEMDYILFI .....RANVTL APNPDEVDEV
RMLY...... .KAPSDGKWG EHELDYLLFI .....VRDVKV QPNPDEVAEI
RILY...... .KAPSDGKWG EHELDYLLFI .....IRDVNL DPNPDEVAEV
RMLY...... .KAPSDGKWG EHEVDYLLFI .....VRDVKL QPNPDEVAEI
RIHY...... .MAPSNEPWG EHEIDYILFY KINAKENLTV NPNVNEVRDF 251                                              300
RYVTQEELRQ MMQ.....PDN GLQWSPWFRI IAARFLERWW ADLDAALNTD
RYVTQEELRQ MMQ.....PDN GLQWSPWFRI IAARFLERWW ADLDAALNTD
KYVSREELKE LVKKADAGEE GLKLSPWFRL VVDNFLMKWW DHVEKGTLVE
KYMNRDDLKE LLRKADAEEE GVKLSPWFRL VVDNFLFKWW DHVEKGSLKD
KYVSREELKE LVKKADAGDE AVKLSPWFRL VVDNFLMKWW DHVEKGTITE
KWVSPNDLKT MF.....ADP SYKFTPWFKI ICENYLFNWW EQLDDLSEVE

301
KHEDWGTVHH INEA*
KHEDWGTVHH INEA*
A.IDMKTIHK L*
A.ADMKTIHK L*
A.ADMKTIHK L*
NDRQ...IHR ML*
```

FIG. 12A

```
  1  ccaaaaacaa ctcaaatctc ctccgtcgct cttactccgc catgggtgac
 51  gactccggca tggatgctgt tcagcgacgt ctcatgtttg acgatgaatg
101  cattttggtg gatgagtgtg acaatgtggt gggacatgat accaaataca
151  attgtcactt gatggagaag attgaaacag gtaaaatgct gcacagagca
201  ttcagcgttt ttctattcaa ttcaaaatac gagttacttc ttcagcaacg
251  gtctgcaacc aaggtgacat ttcctttagt atggaccaac acctgttgca
301  gccatccact ctacagagaa tccgagcttg tccccgaaac gcctgagaga
351  atgctgcaca gaggaxxxxx xxxxxxxxxx xxxxxxxxxx xxxxxxxxxx
401  xxxxxxxxxx xxxxxxxxxx xxxxxxxxxx xxxxxxxxxx xxxxxxxxxx
451  xxxxxxxxxx xxxxxxxxxx xxxxxxxxxx xxxxxxxxxx xxxxxxxxxx
501  xxxxxxxxxx xxxxxxxxxx xxxxxxxxxx xxxxxxxxxx xxxxxxxxxx
551  xxxxxxxxxx xxxxxxxxxx xxxxxxxxxx xxxxxxxxxx xxxxxxxxxx
```

FIG. 12B

```
601  xxxxxxxxxx xxxxxxxxxx xxxxxxxxxx xxxxxxxxxx xxxxxxxxxx
651  xxxxxxxxxx xxxxxxxxxx xxxxxxxxxx tcatgtgcaa aagggtacac
701  tcactgaatg caatttgata tgaaaccat acacaagctg atatagaaac
751  acccctcaa ccgaaaagca agcctaataa ttcgggttgg gtcgggtcta
801  ccatcaattg ttttttcctt ttaacaactt ttaatctcta tttgagcatg
851  ttgattcttg tcttttgtgt gtaagatttt gggtttcgtt tcagttgtaa
901  taatgaacca ttgatggttt gcaatttcaa gttcctatcg acatgtagtg
951  atctaaaaaa
```

```
                                                                                                   70
           1
Plant beta    ........   ...MDTLLKT  PN-LeFl-p-  -HG....F-  vk.-S-f-s-  k---fG--K-  ce--g---vc
A.t. epsilon  MECVGARNFA  AMAVSTFPSW  SCRRKFPVVK  RYSYRNIRFG  LCSVRASGGG  SSGSESCVAV  REDFADEEDF
Consensus     ----------  ----------  -------T--  ---------F  ----------  ----------  --E-------
              Cyanobacterial enzyme begins
           71                                                                                      140
Plant beta    Vk--SsALLe  LVPETKKENL  DFELPmYDp.  ...S.Kg-VV  DLAVGGGPA   GLAVAQQVSE  AGLSVcSIDP
A.t. epsilon  VKAGGSEIL.  FVQMQQNKDM  DEQSKLVDKL  PPISIGDGAL  DHVVIGCGPA  GLALAAESAK  LGLKVGLIGP
Consensus     VK--S--L--  -V--------  D------D--  ---S------  D--V-G-GPA  GLA-A-----  -GL-V--I-P
              Possible subunit interaction domain                        Dinucleotic de-binding signature
           141                                                                                     210
Plant beta    -PKLIWPNN   YGVWDEFEA   MDLLDCLDaT  WSGa-VYi Dd  -t-KDL-RPY  GRVNRKQLKS  KMmQKCI-NG
A.t. epsilon  DLP...FTNN  YGVWEDEFND  LGLQKCIEHV  WRETIVYLDD   DKPITIGRAY  GRVSRRLLHE  ELLRRCVESG
Consensus     --P------   -NN YGVW-DEF--  --L--C---  W----VY-DD   -----R-Y   GRV-R--L--  ----C---G
              Conserved region #1
           211                                                                                     280
Plant beta    VKFHqaKVik  ViHE.E-kSm  liCnDG-tIQ  AtVVLDATGF  SR-.LVQYDK   PYnPGY.QVA  YGIIAEVeeH
A.t. epsilon  VSYLSSKVDS  ITEASDGLRL  VACDDNNVIP  CRLATVASGA  ASGKLLQYEV   GGPRVCVQTA  YGVEVEVENS
Consensus     V------KV-  ----------  --C-D--I--  ----A-G---  -----Q-QY-   ----Q-A     YG---EV---
```

FIG. 13A

```
                281                                                                                           350
Plant beta      PDD--KMVfM  DWRDsHL-nn  -eLKERNs-i   PTFLYAMPFS  SNrIFLEETS  LVARPGLrmd  DIQERMvARL
A.t. epsilon    PYDPDQMVFM  DYRDY..TNE  .KVRSLEAEY   PTFLYAMPMT  KSRLFFEETC  LASKDVMPFD  LLKTKLMRL
Consensus       P-D---MVFM  D-RD----N   -eLKERNs-i   PTFLYAMP--  --R-F-EET-  L-------D   -------RL
                 ↑ Conserved region #2                ↑ Conserved region #3              ↑ Predicted TM helix 351                                                                                           420
Plant beta      -HLGlkvKsI  EEDEhCvIPM  GGpLPVIPQR   VVGiGGTAGm  VHPSTGYMVA  RTLAAAPvVA  NAIi-YLgSe
A.t. epsilon    DTLGIRILKT  YEEEWSYIPV  GGSLPNTEQK   NLAFGAAASM  VHPATGYSVV  RSLSEAPKYA  SVIAEILREE
Consensus       --LGI----   -E-E---IP-  GG-LP---Q-   ---G-A-M    VHP-TGY-V-  R-L--AP--A  -I--L---E
                                         ↑ Conserved region #4

421                                                                                           480
Plant beta      -s-s..G-eL  SaeVWkDLWP  IERRRQREFF   CFGMDILLKL  DLpATRRFFD  AFFDLePrYW
A.t. epsilon    TTKQINSN.I  SRQAWDTLWP  PERKRQRAFF   LFGLALIVQF  DTEGIRSFFR  TFFRLPKWMW
Consensus       --------    S---W--LWP  -ER-RQR-FF   -FG------   D----R-FF-  -FF--L----W
                            ↑ Conserved region #5                                        ↑ Predicted TM helix 481                                                                           533
Plant beta      HGFLSSRRLfL  PELivFGLSL  FShASNTSR-   EIMTK.GT-P  Lv-MINNLIQ  D-e
A.t. epsilon    QGFLGSTLTS   GDLVLFALYM  FVISPNNLRK   GLINHLISDP  TGATMIKTYL  KV.
Consensus       -GFL-S-L--   --L--F-L--  F----N-R-    ---------   ---------   ---
                ↑ Predicted TM helix
```

FIG. 13B

GENES OF CAROTENOID BIOSYNTHESIS AND METABOLISM AND A SYSTEM FOR SCREENING FOR SUCH GENES

BACKGROUND OF THE INVENTION

1. Field of the Invention

The present invention describes the DNA sequence for eukaryotic genes encoding ε, isopentenyl pyrophosphate isomerase (IPP) and β-carotene hydroxylase as well as vectors containing the same and hosts transformed with said vectors. The present invention also provides a method for augmenting the accumulation of carotenoids and production of novel and rare carotenoids. The present invention provides methods for controlling the ratio of various carotenoids in a host. Additionally, the present invention provides a method for screening for eukaryotic genes encoding enzymes of carotenoid biosynthesis and metabolism.

2. Discussion of the Background

Carotenoid pigments with cyclic endgroups are essential components of the photosynthetic apparatus in oxygenic photosynthetic organisms (e.g., cyanobacteria, algae and plants; Goodwin, 1980). The symmetrical bicyclic yellow carotenoid pigment β-carotene (or, in rare cases, the asymmetrical bicyclic α-carotene) is intimately associated with the photosynthetic reaction centers and plays a vital role in protecting against potentially lethal photooxidative damage (Koyama, 1991). β-carotene and other carotenoids derived from it or from α-carotene also serve as light-harvesting pigments (Siefermann-Harms, 1987), are involved in the thermal dissipation of excess light energy captured by the light-harvesting antenna (Demmig-Adams & Adams, 1992), provide substrate for the biosynthesis of the plant growth regulator abscisic acid (Rock & Zeevaart, 1991), and are precursors of vitamin A in human and animal diets (Krinsky, 1987). Plants also exploit carotenoids as coloring agents in flowers and fruits to attract pollinators and agents of seed dispersal (Goodwin, 1980). The color provided by carotenoids is also of agronomic value in a number of important crops. Carotenoids are currently harvested from plants for use as pigments in food and feed.

The probable pathway for formation of cyclic carotenoids in plants, algae and cyanobacteria is illustrated in FIG. 1. Two types of cyclic endgroups are commonly found in higher plant carotenoids, these are referred to as the β and α cyclic endgroups (FIG. 3.; the acyclic endgroup is referred to as the Ψ or psi endgroup). These cyclic endgroups differ only in the position of the double bond in the ring. Carotenoids with two β rings are ubiquitous, and those with one β and one ε ring are common, but carotenoids with two ε rings are rarely detected. β-Carotene (FIG. 1) has two β endgroups and is a symmetrical compound that is the precursor of a number of other important plant carotenoids such as zeaxanthin and violaxanthin (FIG. 2).

Carotenoid enzymes have previously been isolated from a variety of sources including bacteria (Armstrong et al., 1989, Mol. Gen. Genet. 216, 254–268; Misawa et al., 1990, J. Bacteriol., 172, 6704–12), fungi (Schmidhauser et al., 1990, Mol. Cell. Biol. 10, 5064–70), cyanobacteria (Chamovitz et al., 1990, Z. Naturforsch, 45c, 482–86) and higher plants (Bartley et al., Proc. Natl. Acad. Sci USA 88, 6532–36; Martinez-Ferez & Vioque, 1992, Plant Mol. Biol. 18, 981–83). Many of the isolated enzymes show a great diversity in function and inhibitory properties between sources. For example, phytoene desaturases from Synechococcus and higher plants carry out a two-step desaturation to yield ζ-carotene as a reaction product; whereas the same enzyme from Erwinia introduces four double bonds forming lycopene. Similarity of the amino acid sequences are very low for bacterial versus plant enzymes. Therefore, even with a gene in hand from one source, it is difficult to screen for a gene with similar function in another source. In particular, the sequence similarity between prokaryotic and eukaryotic genes is quite low.

Further, the mechanism of gene expression in prokaryotes and eukaryotes appears to differ sufficiently such that one can not expect that an isolated eukaryotic gene will be properly expressed in a prokaryotic host.

The difficulties in isolating related genes is exemplified by recent efforts to isolated the enzyme which catalyzes the formation of β-carotene from the acyclic precursor lycopene. Although this enzyme had been isolated in a prokaryote, it had not been isolated from any photosynthetic organism nor had the corresponding genes been identified and sequenced or the cofactor requirements established. The isolation and characterization of the enzyme catalyzing formation of β-carotene in the cyanobacterium Synechococcus PCC7942 was described by the present inventors and others (Cunningham et al., 1993 and 1994).

The need remains for the isolation of eukaryotic genes involved in the carotenoid biosynthetic pathway, including a gene encoding an ε cyclase, IPP isomerase and β-carotene hydroxylase. There remains a need for methods to enhance the production of carotenoids. There also remains a need in the art for methods for screening for eukaryotic genes encoding enzymes of carotenoid biosynthesis and metabolism.

SUMMARY OF THE INVENTION

Accordingly, a first object of this invention is to provide isolated eukaryotic genes which encode enzymes involved in carotenoid biosynthesis; in particular, ε cyclase, IPP isomerase and β-carotene hydroxylase.

A second object of this invention is to provide eukaryotic genes which encode enzymes which produce novel carotenoids.

A third object of the present invention is to provide vectors containing said genes.

A fourth object of the present invention is to provide hosts transformed with said vectors.

Another object of the present invention is to provide hosts which accumulates novel or rare carotenoids or which overexpress known carotenoids.

Another object of the present invention is to provide hosts with inhibited carotenoid production.

Another object of this invention is to secure the expression of eukaryotic carotenoid-related genes in a recombinant prokaryotic host.

A final object of the present invention is to provide a method for screening for eukaryotic genes which encode enzymes involved in carotenoid biosynthesis and metabolism.

These and other objects of the present invention have been realized by the present inventors as described below.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a DNA sequence and the predicted amino acid sequence of ε cyclase isolated from A. thaliana (SEQ ID NOS: 1 and 2). These sequences were deposited under Genbank accession number U50738. This cDNA is incorporated into the plasmid pATeps.

FIG. 5 is a DNA sequence encoding the β-carotene hydroxylase isolated from A. thaliana (SEQ ID NO: 3). This cDNA is incorporated into the plasmid pATOHB.

FIG. 6 is an alignment of the predicted amino acid sequences of A. thaliana β-carotene hydroxylase (SEQ ID NO: 4) with the bacterial enzymes from Alicalgenes sp. (SEQ ID NO: 5) (Genbank D58422), Erwinia herbicola Eho10 (SEQ ID NO.: 6) (GenBank M872280), Erwinia uredovora (SEQ ID NO.: 7) (GenBank D90087) and Agrobacterium aurianticum (SEQ ID NO.: 8) (GenBank D58420). A consensus sequence is also shown. Consensus is identical for all five genes where a capital letter appears. A lowercase letter indicates that three of five, including A. thaliana, have the identical residue. TM; transmembrane FIG. 7 is a DNA sequence of a cDNA encoding an IPP isomerase isolated from A. thaliana (SEQ ID NO: 9). This cDNA is incorporated into the plasmid pATDP5.

FIG. 8 is a DNA sequence of a second cDNA encoding another IPP isomerase isolated from A. thaliana (SEQ ID NO: 10). This cDNA is incorporated into the plasmid pATDP7.

FIG. 9 is a DNA sequence of a cDNA encoding an IPP isomerase isolated from Haematococcus pluvialis (SEQ ID NO: 11). This cDNA is incorporated into the plasmid pHP04.

FIG. 10 is a DNA sequence of a second cDNA encoding another IPP isomerase isolated from Haematococcus pluvialis (SEQ ID NO: 12). This cDNA is incorporated into the plasmid pHP05.

FIG. 11 is an alignment of the predicted amino acid sequences of the IPP isomerase isolated from A. thaliana (SEQ ID NO.: 16 and 18), H. pluvialis (SEQ ID NOS.: 14 and 15), Clarkia breweri (SEQ ID NO.: 17) (See, Blanc & Pichersky, Plant Physiol. (1995) 108:855; Genbank accession no. X82627) and Saccharomyces cerevisiae (SEQ ID NO.: 19) (Genbank accession no. J05090).

FIG. 12 is a DNA sequence of the cDNA encoding an IPP isomerase isolated from marigold (SEQ ID NO: 13). This cDNA is incorporated into the plasmid pPMDP1. xxx's denote a region not yet sequenced at the time when this application was prepared.

FIG. 13 is an alignment of the consensus sequence of 4 plant β-cyclases (SEQ ID NO.: 20) with the A. thaliana ε-cyclase (SEQ ID No.: 21). A capital letter in the plant β consensus is used where all 4 β cyclase genes predict the same amino acid residue in this position. A small letter indicates that an identical residue was found in 3 of the 4. Dashes indicate that the amino acid residue was not conserved and dots in the sequence denote a gap. A consensus for the aligned sequences is given, in capital letters below the alignment, where the β and ε cyclase have the same amino acid residue. Arrows indicate some of the conserved amino acids that will be used as junction sites for construction of chimeric cyclases with novel enzymatic activities. Several regions of interest including a sequence signature indicative of a dinucleotide-binding motif and 2 predicted transmembrane (TM) helical regions are indicated below the alignment and are underlined.

DESCRIPTION OF THE PREFERRED EMBODIMENTS

Isolated eukaryotic genes which encode enzymes involved in carotenoid biosynthesis The present inventors have now isolated eukaryotic genes encoding ε and β-carotene hydroxylase from A. thaliana and IPP isomerases from several sources.

The present inventors have now isolated the eukaryotic gene encoding the enzyme IPP isomerase which catalyzes the conversion of isopentenyl pyrophosphate (IPP) to dimethylallyl pyrophosphate (DMAPP). IPP isomerases were isolated from A. thaliana, H. pluvialis and marigold.

Alignments of these are shown in FIG. 12 (excluding the marigold sequence). Plasmids containing these genes were deposited with the American Type Culture Collection, 12301 Parklawn Drive, Rockville Md. 20852 on Mar. 4, 1996 under ATCC accession numbers 98000 (pHP05-H. pluvialis); 98001 (pMDP1-marigold); 98002 (pATDP7-H. pluvialis) and 98004 (pHP04-H. pluvialis).

The present inventors have also isolated the gene encoding the enzyme, ε cyclase, which is responsible for the formation of ε endgroups in carotenoids. A gene encoding an ε cyclase from any organism has not heretofore been described. The A. thaliane ε-cyclase adds an ε-ring to only one end of the symmetrical lycopene while the related β-cyclase adds a ring at both ends. The DNA of the present invention is shown in FIG. 4 and SEQ ID NO: 1. A plasmid containing this gene was deposited with the American Type Culture Collection, 12301 Parklawn Drive, Rockville Md. 20852 on Mar. 4, 1996 under ATCC accession number 98005 (pATeps -A. thaliana).

The present inventors have also isolated the gene encoding the enzyme, β-carotene hydroxylase, which is responsible for hydroxylating the β endgroup in carotenoids. The DNA of the present invention is shown in SEQ ID NO: 3 and FIG. 5. The full length gene product hydroxylates both end groups of β-carotene as do products of genes which encode proteins truncated by up to 50 amino acids from the N-terminus. Products of genes which encode proteins truncated between about 60–110 amino acids from the N-terminus preferentially hydroxylates only one ring. A plasmid containing this gene was deposited with the American Type Culture Collection, 12301 Parklawn Drive, Rockville Md. 20852 on Mar. 4, 1996 under ATCC accession number 98003 (pATOHB-*A. thaliana*).

Eukaryotic genes which encode enzymes which produce novel or rare carotenoids

Figure 1:
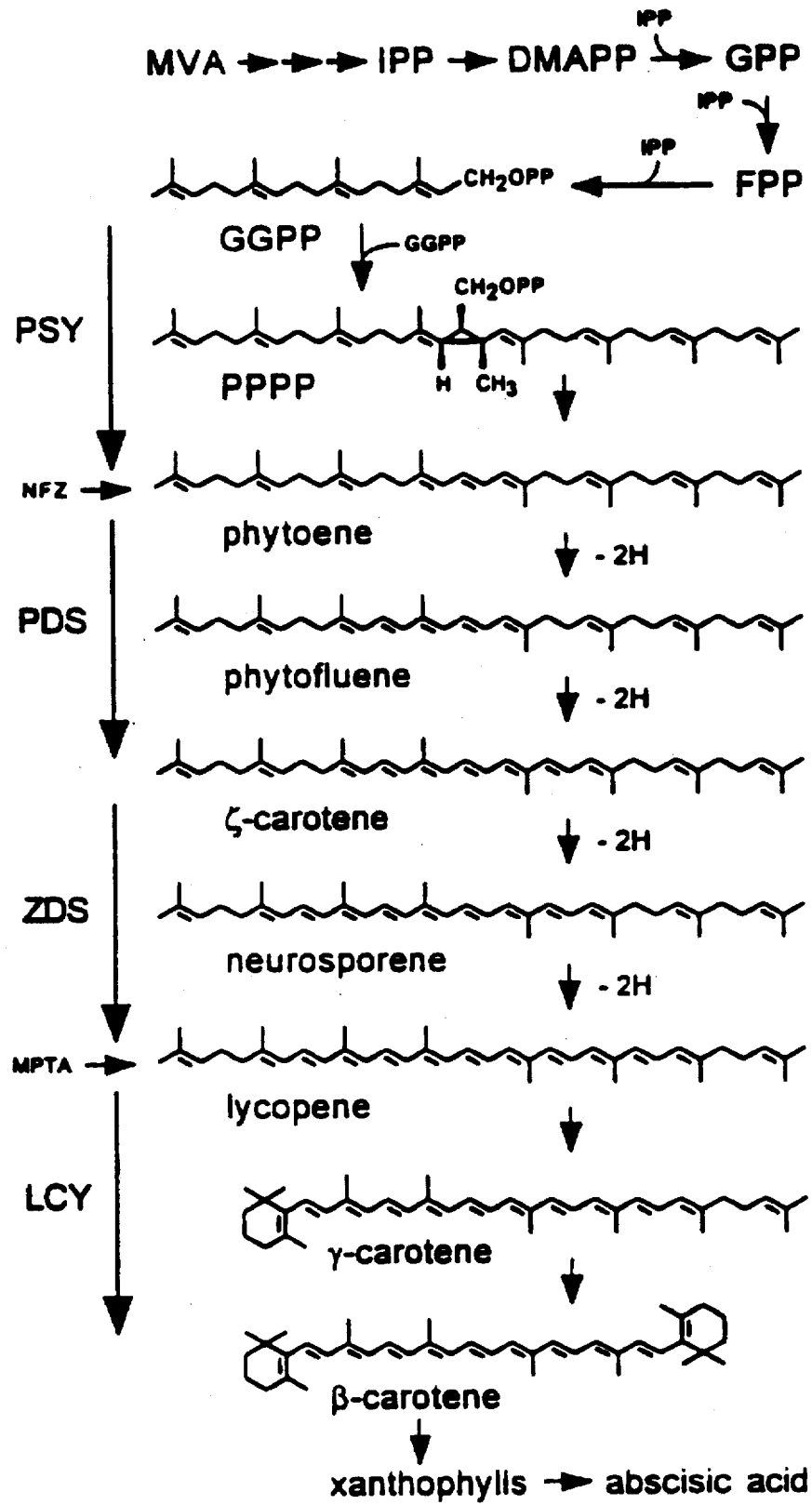
FIG. 1 is a schematic representation of the pathway of β-carotene biosynthesis in cyanobacteria, algae and plants. The enzymes catalyzing various steps are indicated at the left. Target sites of the bleaching herbicides NFZ and MPTA are also indicated at the left. Abbreviations: DMAPP, dimethylallyl pyrophosphate; FPP, farnesyl pyrophosphate; GGPP, geranylgeranyl pyrophosphate; GPP, geranyl pyrophosphate; IPP, isopentenyl pyrophosphate; LCY, lycopene cyclase; MVA, mevalonic acid; MPTA, 2-(4-methylphenoxy)triethylamine hydrochloride; NFZ, norflurazon; PDS, phytoene desaturase; PSY, phytoene synthase; ZDS, ζ-carotene desaturase; PPPP, prephytoene pyrophosphate.
Figure 2A:
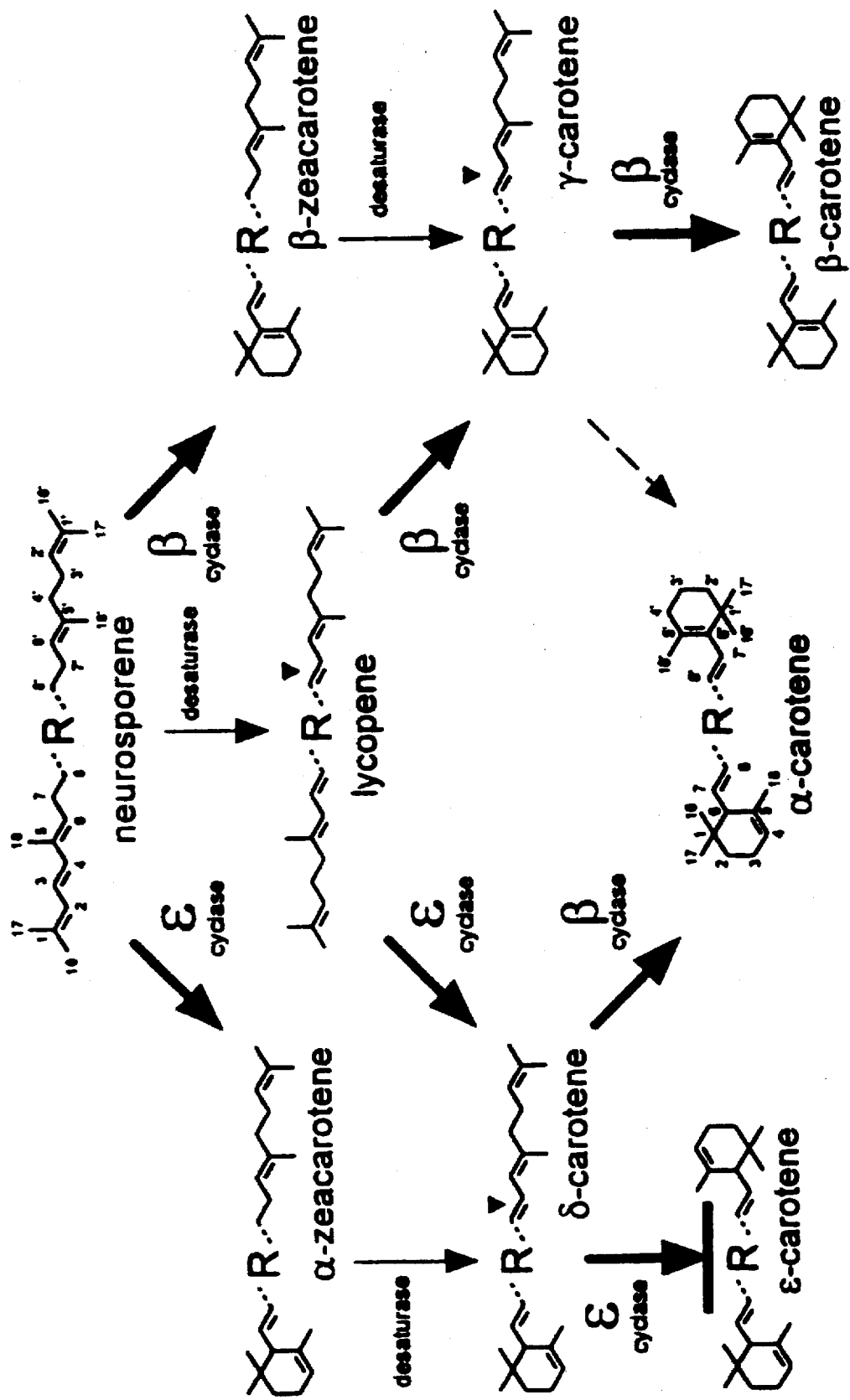
FIG. 2 depicts possible routes of synthesis of cyclic carotenoids and common plant and algal xanthophylls (oxycarotenoids) from neurosporene. Demonstrated activities of the β- and ε-cyclase enzymes of A. thaliana are indicated by bold arrows labelled with β or ε respectively. A bar below the arrow leading to ε-carotene indicates that the enzymatic activity was examined but no product was detected. The steps marked by an arrow with a dotted line have not been specifically examined. Conventional numbering of the carbon atoms is given for neurosporene and α-carotene. Inverted triangles (▼) mark positions of the double bonds introduced as a consequence of the desaturation reactions.
Figure 2B:
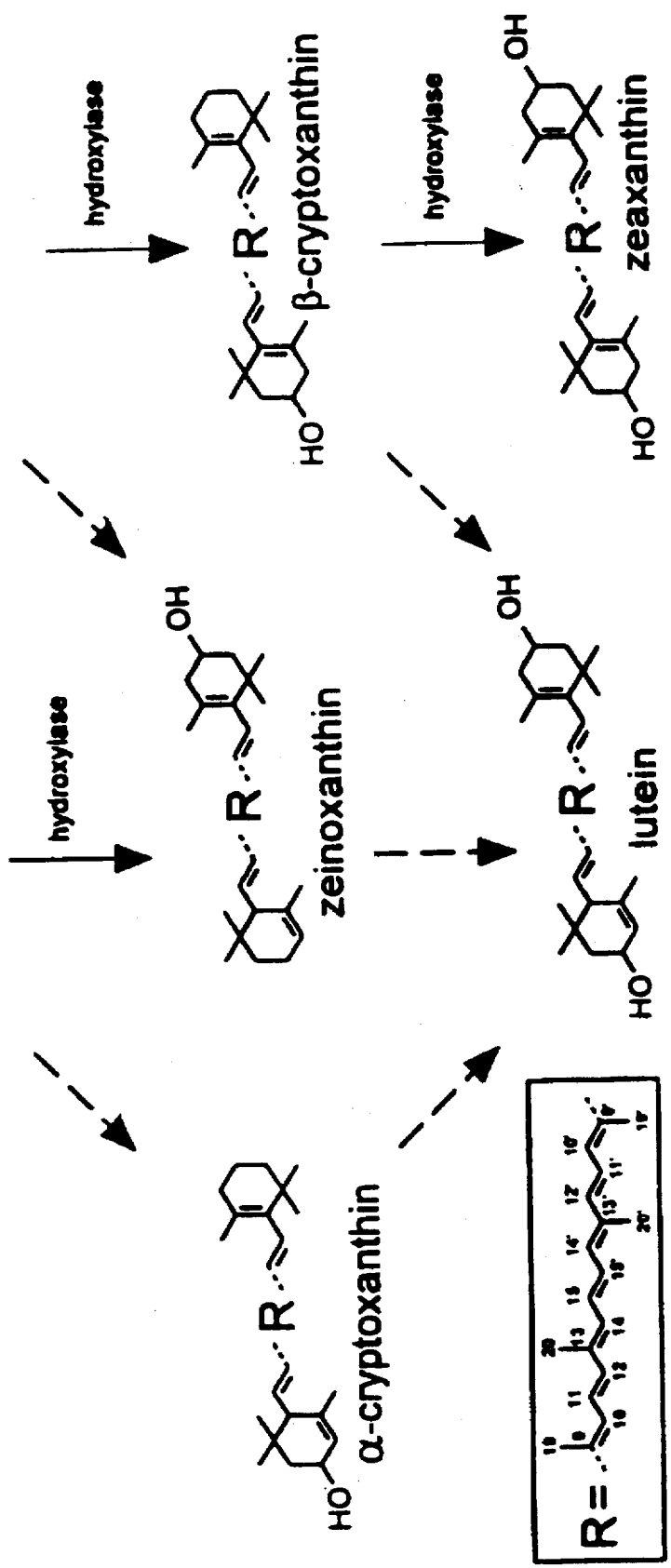
Figure 3:
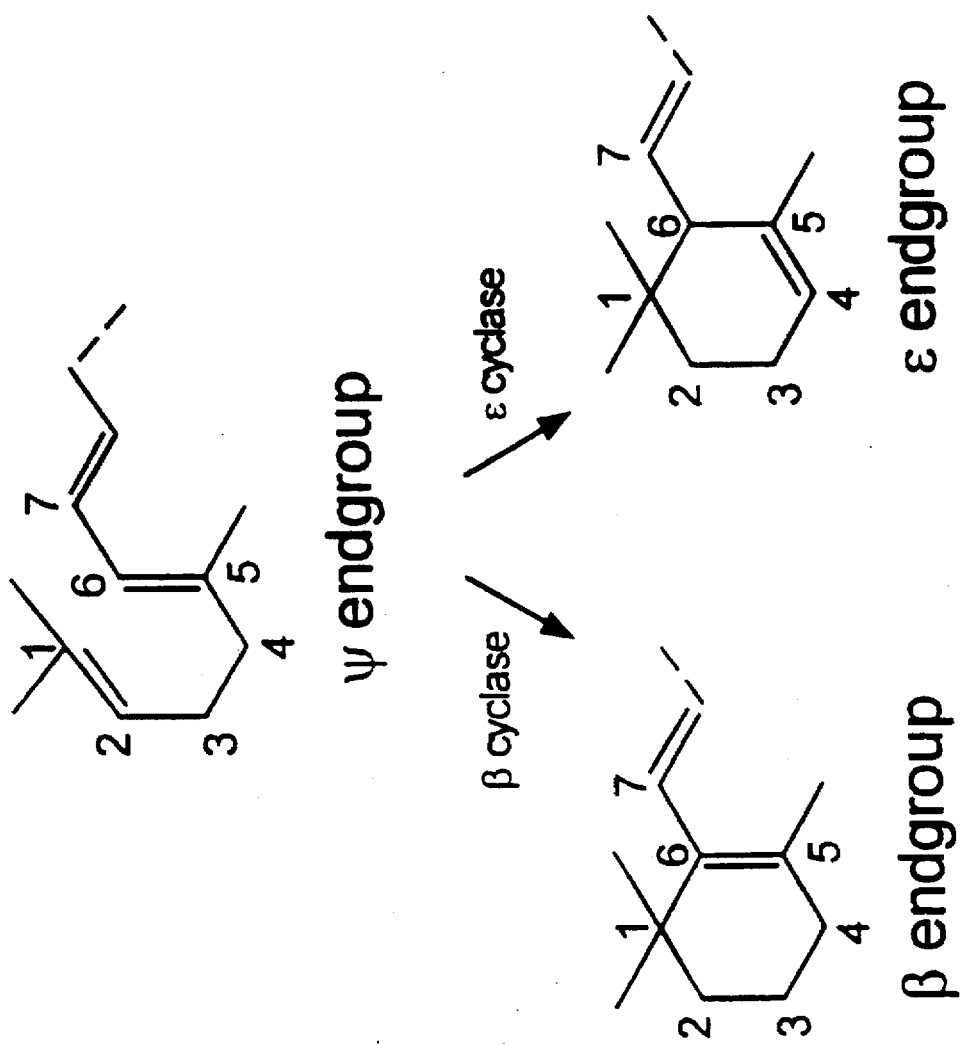
FIG. 3 depicts the carotene endgroups which are found in plants.

The present invention also relates to novel enzymes which can transform known carotenoids into novel or rare products. That is, currently ε-carotene (see FIG. 2) and γ-carotene can only be isolated in minor amounts. As described below, an enzyme can be produced which would transform lycopene to γ-carotene and lycopene to ε-carotene. With these products in hand, bulk synthesis of other carotenoids derived from them are possible. For example, ε-carotene can be hydroxylated to form an isomer of lutein (1 ε- and 1 β-ring) and zeaxanthin (2 β-rings) where both endgroups are, instead, ε-rings.

The eukaryotic genes in the carotenoid biosynthetic pathway differ from their prokaryotic counterparts in their 5' region. As used herein, the 5' region is the region of eukaryotic DNA which precedes the initiation codon of the counterpart gene in prokaryotic DNA. That is, when the consensus areas of eukaryotic and prokaryotic genes are aligned, the eukaryotic genes contain additional coding sequences upstream of the prokaryotic initiation codon.

The present inventors have found that the amount of the 5' region present can alter the activity of the eukaryotic enzyme. Instead of diminishing activity, truncating the 5' region of the eukaryotic gene results in an enzyme with a different specificity. Thus, the present invention relates to enzymes which are truncated to within 0–50, preferably 0–25, codons of the 5' initiation codon of their prokaryotic counterparts as determined by alignment maps.

For example, as discussed above, when the gene encoding *A. thaliana* β-carotene hydroxylase was truncated, the resulting enzyme catalyzed the formation of β-cryptoxanthin as major product and zeaxanthin as minor product; in contrast to its normal production of zeaxanthin.

In addition to novel enzymes produced by truncating the 5' region of known enzymes, novel enzymes which can participate in the formation of novel carotenoids can be formed by replacing portions of one gene with an analogous sequence from a structurally related gene. For example, β-cyclase and ε-cyclase are structurally related (see FIG. 13). By replacing a portion of β-lycopene cyclase with the analogous portion of ε-cyclase, an enzyme which produces γ-carotene will be produced (1 endgroup). Further, by replacing a portion of the ε-lycopene cyclase with the analogous portion of β-cyclase, an enzyme which produces ε-carotene will be produced (ε-cyclase normally produces a compound with 1 ε-endgroup (δ-carotene) not 2). Similarly, β-hydroxylase could be modified to produce enzymes of novel function by creation of hybrids with ε-hydroxylase.

Vectors

The genes encoding the carotenoid enzymes as described above, when cloned into a suitable expression vector, can be used to overexpress these enzymes in a plant expression system or to inhibit the expression of these enzymes. For example, a vector containing the gene encoding ε-cyclase can be used to increase the amount of α-carotene in an organism and thereby alter the nutritional value, pharmacology and visual appearance value of the organism.

In a preferred embodiment, the vectors of the present invention contain a DNA encoding an eukaryotic IPP isomerase upstream of a DNA encoding a second eukaryotic carotenoid enzyme. The inventors have discovered that inclusion of an IPP isomerase gene increases the supply of substrate for the carotenoid pathway; thereby enhancing the production of carotenoid endproducts. This is apparent from the much deeper pigmentation in carotenoid-accumulating colonies of *E. coli* which also contain one of the aforementioned IPP isomerase genes when compared to colonies that lack this additional IPP isomerase gene. Similarly, a vector comprising an IPP isomerase gene can be used to enhance production of any secondary metabolite of dimethylallyl pyrophosphate (such as isoprenoids, steroids, carotenoids, etc.).

Alternatively, an anti-sense strand of one of the above genes can be inserted into a vector. For example, the ε-cyclase gene can be inserted into a vector and incorporated into the genomic DNA of a host, thereby inhibiting the synthesis of ε,β carotenoids (lutein and α-carotene) and enhancing the synthesis of β,β carotenoids (zeaxanthin and β-carotene).

Suitable vectors according to the present invention comprise a eukaryotic gene encoding an enzyme involved in carotenoid biosynthesis or metabolism and a suitable promoter for the host can be constructed using techniques well known in the art (for example Sambrook et al., *Molecular Cloning A Laboratory Manual*, Cold Spring Harbor Laboratory, Cold Spring Harbor, N.Y., 1989).

Suitable vectors for eukaryotic expression in plants are described in Frey et al., Plant J. (1995) 8(5):693 and Misawa et al, 1994a; incorporated herein by reference.

Suitable vectors for prokaryotic expression include pACYC184, pUC119, and pBR322 (available from New England BioLabs, Beverly, Mass.) and pTreHis (Invitrogen) and pET28 (Novagene) and derivatives thereof.

The vectors of the present invention can additionally contain regulatory elements such as promoters, repressors selectable markers such as antibiotic resistance genes, etc.

Hosts

Host systems according to the present invention can comprise any organism that already produces carotenoids or which has been genetically modified to produce carotenoids. The IPP isomerase genes are more broadly applicable for enhancing production of any product dependent on DMAPP as a precursor.

Organisms which already produce carotenoids include plants, algae, some yeasts, fungi and cyanobacteria and other photosynthetic bacteria. Transformation of these hosts with vectors according to the present invention can be done using standard techniques such as those described in Misawa et al., (1990) supra; Hundle et al., (1991) Photchem. Photobiol. 54, 89–93; both incorporated herein by reference.

Alternatively, transgenic organisms can be constructed which include the DNA sequences of the present invention (Bird et al, 1991; Bramley et al, 1992; Misawa et al, 1994a; Misawa et al, 1994b; Cunningham et al, 1993). The incorporation of these sequences can allow the controlling of carotenoid biosynthesis, content, or composition in the host cell. These transgenic systems can be constructed to incorporate sequences which allow over-expression of the carotenoid genes of the present invention. Transgenic systems can also be constructed containing antisense expression of the DNA sequences of the present invention. Such antisense expression would result in the accumulation of the substrates of the substrates of the enzyme encoded by the sense strand.

A method for screening for eukaryotic genes which encode enzymes involved in carotenoid biosynthesis The method of the present invention comprises transforming a prokaryotic host with a DNA which may contain a eukaryotic or prokaryotic carotenoid biosynthetic gene; culturing said transformed host to obtain colonies; and screening for colonies exhibiting a different color than colonies of the untransformed host.

Suitable hosts include *E. coli*, cyanobacteria such as Synechococcus and Synechocystis, alga and plant cells. *E. coli* are preferred.

In a preferred embodiment, the above "color complementation test" can be enhanced by using mutants which are either (1) deficient in at least one carotenoid biosynthetic gene or (2) overexpress at least one carotenoid biosynthetic gene. In either case, such mutants will accumulate carotenoid precursors.

Prokaryotic and eukaryotic DNA libraries can be screened in total for the presence of genes of carotenoid biosynthesis, metabolism and degradation. Preferred organisms to be screened include photosynthetic organisms.

*E. coli* can be transformed with these eukaryotic cDNA libraries using conventional methods such as those described in Sambrook et al, 1989 and according to protocols described by the venders of the cloning vectors.

For example, the cDNA libraries in bacteriophage vectors such as lambdaZAP (Stratagene) or lambdaZIPOLOX (Gibco BRL) can be excised en masse and used to transform *E. coli* can be inserted into suitable vectors and these vectors can the be used to transform *E. coli*. Suitable vectors include pACYC184, pUC119, pBR322 (available from New England BioLabs, Beverly, Mass.). pACYC is preferred.

Transformed *E. coli* can be cultured using conventional techniques. The culture broth preferably contains antibiotics to select and maintain plasmids. Suitable antibiotics include penicillin, ampicillin, chloramphenicol, etc. Culturing is typically conducted at 20°–40° C., preferably at room temperature (20°–25° C.), for 12 hours to 7 days.

Cultures are plated and the plates are screened visually for colonies with a different color than the colonies of the untransformed host *E. coli*. For example, *E. coli* transformed with the plasmid, pAC-BETA (described below), produce yellow colonies that accumulate β-carotene. After transformation with a cDNA library, colonies which contain a different hue than those formed by *E. coli*/pAC-BETA would be expected to contain enzymes which modify the structure or degree of expression of β-carotene. Similar standards can be engineered which overexpress earlier products in carotenoid biosynthesis, such as lycopene, γ-carotene, etc.

Having generally described this invention, a further understanding can be obtained by reference to certain specific examples which are provided herein for purposes of illustration only and are not intended to be limiting unless otherwise specified.

EXAMPLE

I. Isolation of β-carotene hydroxylase

Plasmid Construction

An 8.6 kb BglII fragment containing the carotenoid biosynthetic genes of *Erwinia herbicola* was first cloned in the BamHI site of plasmid vector pACYC184 (chloramphenicol resistant), and then a 1.1 kb BamHI fragment containing the β-carotene hydroxylase (CrtZ) was deleted. The resulting plasmid, pAC-BETA, contains all the genes for the formation of β-carotene. *E. coli* strains containing this plasmid accumulate β-carotene and form yellow colonies (Cunningham et al., 1994).

A full length gene encoding IPP isomerase of *Haematococcus pluvialis* (HP04) was first cut out with BamHI-KpnI from pBluescript SK+, and then cloned into a pTrcHisA vector with high-level expression from the trc promoter (Invitrogen Inc.). A fragment containing the IPP isomerase and trc promoter was excised with EcoRV-KpnI and cloned in HindIII site of PAC-BETA. *E. coli* cells transformed with this new plasmid pAC-BETA-04 form orange (deep yellow) colonies on LB plates and accumulate more β-carotene than cells that contain pAC-BETA.

Screening of the Arabidopsis cDNA Library

Several λ cDNA expression libraries of Arabidopsis were obtained from the Arabidopsis Biological Resource Center (Ohio State University, Columbus, Ohio) (Kieber et al., 1993). The λ cDNA libraries were excised in vivo using Stratagene's ExAssist SOLR system to produce a phagemid cDNA library wherein each clone also contained an amphicillin.

*E. coli* strain DH10BZIP was chosen as the host cells for the screening and pigment production. DH10B cells were transformed with plasmid pAC-BETA-04 and were plated on LB agar plates containing chloramphenicol at 50 μg/ml (from United States Biochemical Corporation). The phagemid Arabidopsis cDNA library was then introduced into DH10B cells already containing pAC-BETA-04. Transformed cells containing both pAC-BETA-04 and Arabidopsis cDNA were selected on chloramphenicol plus ampicillin (150 μg/ml) agar plates. Maximum color development occurred after 5 days incubation at room temperature, and lighter yellow colonies were selected. Selected colonies were inoculated into 3 ml liquid LB medium containing ampicillin and chloramphenicol, and cultures were incubated. Cells were then pelleted and extracted in 80 μl 100% acetone in microfuge tubes. After centrifugation, pigmented supernatant was spotted on silica gel thin-layer chromatography (TLC) plates, and developed with a hexane; ether (1:1) solvent system. β-carotene hydroxylase clones were identified based on the appearance of zeaxanthin on TLC plate.

Subcloning and Sequencing

The β-carotene hydroxylase cDNA was isolated by standard procedures (Sambrook et al., 1989). Restriction maps showed that three independent inserts (1.9 kb, 0.9 kb and 0.8 kb) existed in the cDNA. To determine which cDNA insert confers the β-carotene hydroxylase activity, plasmid DNA was digested with NotI (a site in the adaptor of the cDNA library) and three inserts were subcloned into NotI site of SK vectors. These subclones were used to transform *E. coli* cells containing pAC-BETA-04 again to test the hydroxylase activity. A fragment of 0.95 kb, later shown to contain the hydroxylase gene, was also blunt-ended and cloned into pTrcHis A,B,C vectors. To remove the N terminal sequence, a restriction site (BglII) was used that lies just before the conserved sequence with bacterial genes. A BglII-XhoI fragment was directionally cloned in BamHI-XhoI digested trc vectors. Functional clones were identified by the color complementation test. A β-carotene hydroxylase enzyme produces a colony with a lighter yellow color than is found in cells containing pAC-BETA-04 alone.

Arabidopsis β-carotene hydroxylase was sequenced completely on both strands on an automatic sequencer (Applied Biosystems, Model 373A, Version 2.0.1S).

Pigment Analysis

A single colony was used to inoculate 50 ml of LB containing ampicillin and chloramphenicol in a 250-ml flask. Cultures were incubated at 28° C. for 36 hours with gentle shaking, and then harvested at 5000 rpm in an SS-34 rotor. The cells were washed once with distilled $H_2O$ and resuspended with 0.5 ml of water. The extraction procedures and HPLC were essentially as described previously (Cunningham et al, 1994).

II. Isolation of ε cyclase

Plasmid Construction

Construction of plasmids PAC-LYC, PAC-NEUR, and pAC-ZETA is described in Cunningham et al., (1994). In brief, the appropriate carotenoid biosynthetic genes from *Erwinia herbicola, Rhodobacter capsulatus,* and Synechococcus sp. strain PCC7942 were cloned in the plasmid vector pACYC184 (New England BioLabs, Beverly, Mass.). Cultures of *E. coli* containing the plasmids PAC-ZETA, pAC-NEUR, and pAC-LYC, accumulate ζ-carotene, neurosporene, and lycopene, respectively. The plasmid PAC-ZETA was constructed as follows: an 8.6-kb BglII fragment containing the carotenoid biosynthetic genes of *E. herbicola* (GenBank M87280; Hundle et al., 1991) was obtained after partial digestion of plasmid pPL376 (Perry et al., 1986; Tuveson et al., 1986) and cloned in the BamHI site of pACYC184 to give the plasmid pAC-EHER. Deletion of adjacent 0.8- and 1.1-kb BamHI-BamHI fragments (deletion Z in Cunningham et al., 1994), and of a 1.1 kB SalI-SalI fragment (deletion X) served to remove most of the coding regions for the *E. herbicola* β-carotene hydroxylase (crt gene) and zeaxanthin glucosyltransferase (crtX gene), respectively. The resulting plasmid, pAC-BETA, retains functional genes for geranylgeranyl pyrophosphate synthase (crtE), phytoene synthase (crtB), phytoene desaturase (crtI), and lycopene cyclase (crtY). Cells of *E. coli* containing this plasmid form yellow colonies and accumulate β-carotene. A plasmid containing both the ε- and β-cyclase cDNAs of *A. thaliana* was constructed by excising the ε in clone y2 as a PvuI-PvuII fragment and ligating this piece in the SnaBI site of a plasmid (pSPORT 1 from GIBCO-BRL) that already contained the β cyclase.

Organisms and Growth Conditions

*E. coli* strains TOP10 and TOP10 F' (obtained from Invitrogen Corporation, San Diego, Calif.) and XL1-Blue (Stratagene) were grown in Luria-Bertani (LB) medium (Sambrook et al., 1989) at 37° C. in darkness on a platform shaker at 225 cycles per min. Media components were from Difco (yeast extract and tryptone) or Sigma (NaCl). Ampicillin at 150 µg/mL and/or chloramphenicol at 50 µ/mL (both from United States Biochemical Corporation) were used, as appropriate, for selection and maintenance of plasmids.

Mass Excision and Color Complementation Screening of an *A. thaliana* cDNA Library A size-fractionated 1–2 kB cDNA library of *A. thaliana* in lambda ZAPII (Kieber et al., 1993) was obtained from the Arabidopsis Biological Resource Center at The Ohio State University (stock number CD4-14). Other size fractionated libraries were also obtained (stock numbers CD4-13, CD4-15, and CD4-16). An aliquot of each library was treated to cause a mass excision of the cDNAs and thereby produce a phagemid library according to the instructions provided by the supplier of the cloning vector (Stratagene; *E. coli* strain XL1-Blue and the helper phage R408 were used). The titre of the excised phagemid was determined and the library was introduced into a lycopene-accumulating strain of *E. coli* TOP10 F' (this strain contained the plasmid pAC-LYC) by incubation of the phagemid with the *E. coli* cells for 15 min at 37° C. Cells had been grown overnight at 30° C. in LB medium supplemented with 2% (w/v) maltose and 10 mM MgSO$_4$ (final concentration), and harvested in 1.5 ml microfuge tubes at a setting of 3 on an Eppendorf microfuge (5415C) for 10 min. The pellets were resuspended in 10 mM MgSO$_4$ to a volume equal to one-half that of the initial culture volume. Transformants were spread on large (150 mm diameter) LB agar petri plates containing antibiotics to provide for selection of cDNA clones (ampicillin) and maintenance of pAC-LYC (chloramphenicol). Approximately 10,000 colony forming units were spread on each plate. Petri plates were incubated at 37° C. for 16 hr and then at room temperature for 2 to 7 days to allow maximum color development. Plates were screened visually with the aid of an illuminated 3× magnifier and a low power stage-dissecting microscope for the rare, pale pinkish-yellow to deep-yellow colonies that could be observed in the background of pink colonies. A colony color of yellow or pinkish-yellow was taken as presumptive evidence of a cyclization activity. These yellow colonies were collected with sterile toothpicks and used to inoculate 3 ml of LB medium in culture tubes with overnight growth at 37° C. and shaking at 225 cycles/min. Cultures were split into two aliquots in microfuge tubes and harvested by centrifugation at a setting of 5 in an Eppendorf 5415C microfuge. After discarding the liquid, one pellet was frozen for later purification of plasmid DNA. To the second pellet was added 1.5 ml EtOH, and the pellet was resuspended by vortex mixing, and extraction was allowed to proceed in the dark for 15–30 min with occasional remixing. Insoluble materials were pelleted by centrifugation at maximum speed for 10 min in a microfuge. Absorption spectra of the supernatant fluids were recorded from 350–550 nm with a Perkin Elmer lambda six spectrophotometer.

Analysis of isolated clones

Eight of the yellow colonies contained β-carotene indicating that a single gene product catalyzes both cyclizations required to form the two β endgroups of the symmetrical β-carotene from the symmetrical precursor lycopene. One of the yellow colonies contained a pigment with the spectrum characteristic of δ-carotene, a monocyclic carotenoid with a single ε endgroup. Unlike the β cyclase, this ε cyclase appears unable to carry out a second cyclization at the other end of the molecule.

The observation that ε is unable to form two cyclic ε endgroups (e.g. the bicyclic ε-carotene) illuminates the mechanism by which plants can coordinate and control the flow of substrate into carotenoids derived from β-carotene versus those derived from α-carotene and also can prevent the formation of carotenoids with two ε endgroups.

The availability of the *A. thaliana* gene encoding the ε cyclase enables the directed manipulation of plant and algal species for modification of carotenoid content and composition. Through inactivation of the ε cyclase, whether at the gene level by deletion of the gene or by insertional inactivation or by reduction of the amount of enzyme formed (by such as antisense technology), one may increase the formation of β-carotene and other pigments derived from it. Since vitamin A is derived only from carotenoids with β endgroups, an enhancement of the production of β-carotene versus α-carotene may enhance nutritional value of crop plants. Reduction of carotenoids with ε endgroups may also be of value in modifying the color properties of crop plants and specific tissues of these plants. Alternatively, where production of α-carotene, or pigments such as lutein that are derived from α-carotene, is desirable, whether for the color properties, nutritional value or other reason, one may overexpress the ε or express it in specific tissues. Wherever agronomic value of a crop is related to pigmentation provided by carotenoid pigments the directed manipulation of expression of the ε gene and/or production of the enzyme may be of commercial value.

The predicted amino acid sequence of the *A. thaliana* ε cyclase enzyme was determined. A comparison of the amino acid sequences of the β and ε enzymes of *Arabidopsis thaliana* (FIG. 13) as predicted by the DNA sequence of the respective genes (FIG. 4 for the ε cDNA sequence), indicates that these two enzymes have many regions of sequence similarity, but they are only about 37% identical overall at the amino acid level. The degree of sequence identity at the DNA base level, only about 50%, is sufficiently low such that we and others have been unable to detect this gene by hybridization using the β cyclase as a probe in DNA gel blot experiments.

REFERENCES

Bird et al, (1991) Biotechnology 9, 635–639.
Bishop et al., (1995) FEBS Lett. 367, 158–162.
Bramley, P. M. (1985) Adv. Lipid Res. 21, 243–279.
Bramley, P. M. (1992) Plant J. 2, 343–349.
Britton, G. (1988). Biosynthesis of carotenoids. In Plant Pigments, T. W. Goodwin, ed. (London: Academic Press), pp. 133–182.
Britton, G. (1979) Z. Naturforsch. Section C Biosci. 34, 979–985.
Britton, G. (1995) UV/Visible spectroscopy. In Carotenoids, Vol. IB: Spectroscopy, G. Britton, S. Liaaen-Jensen, H. P. Pfander, eds. (Basel: Birkhauser Verlag), pp. 13–62.
Bouvier et al., (1994) Plant J. 6, 45–54.
Cunningham et al., (1985) Photochem. Photobiol. 42: 295–307
Cunningham et al., (1993) FEBS Lett. 328, 130–138.
Cunningham et al., (1994) Plant Cell 6, 1107–1121.
Davies, B. H. (1976). Carotenoids. In Chemistry and Biochemistry of Plant Pigments, Vol. 2, T. W. Goodwin, ed (New York: Academic Press), pp. 38–165.
Del Sal et al., (1988). Nucl. Acids Res. 16, 9878.
Demmig-Adams & Adams, (1992) Ann. Rev. Plant Physiol. Mol. Biol. 43, 599–626.
Enzell & Back, (1995) Mass spectrometry. In Carotenoids, Vol. IB: Spectroscopy, G. Britton, S. Liaaen-Jensen, H. P. Pfander, eds. (Basel: Birkhauser Verlag), pp. 261–320.
Frank & Cogdell (1993) Photochemistry and function of carotenoids in photosynthesis. In Carotenoids in Photosynthesis. A. Young and G. Britton, eds. (London: Chapman and Hall). pp. 253–326.
Goodwin, T. W. (1980). The Biochemistry of the Carotenoids. 2nd ed, Vol. 1 (London: Chapman and Hall.
Horvath et al., (1972) Phytochem. 11, 183–187.
Hugueney et al., (1995) Plant J. 8, 417–424.
Hundle et al., (1991) Photochem. Photobiol. 54, 89–93.
Jensen & Jensen, (1971) Methods Enzymol. 23, 586–602.
Kargl & Quackenbush, (1960) Archives Biochem. Biophys. 88, 59–63.
Kargl et al., (1960) Proc. Am. Hort. Soc. 75, 574–578.
Kieber et al., (1993) Cell 72, 427–441.
Koyama, Y. (1991) J. Photochem. Photobiol., B, 9, 265–80.
Krinsky, N. I. (1987) Medical uses of carotenoids. In Carotenoids, N. I. Krinsky, M. M. Mathews-Roth, and R. F. Taylor, eds. (New York: Plenum), pp. 195–206.
Kyte & Doolittle, (1982) J. Mol. Biol. 157, 105–132.
LaRossa & Schloss, (1984) J. Biol. Chem. 259, 8753–8757.
Misawa et al., (1994a) Plant J. 6, 481–489.
Misawa et al., (1994b) J. Biochem, Tokyo, 116, 980–985.
Norris et al., (1995) Plant Cell 7, 2139–2149.
Pecker et al., (1996) Submitted to Plant Mol. Biol.
Perry et al., (1986) J. Bacteriol. 168, 607–612.
Persson & Argos, (1994) J. Mol. Biol. 237, 182–192.
Plumley & Schmidt, (1987) Proc. Nat. Acad. Sci. USA 83, 146–150.
Plumley & Schmidt, (1995) Plant Cell 7, 689–704.
Rossmann et al., (1974) Nature 250, 194–199.
Rock & Zeevaart (1991) Proc. Nat. Acad. Sci. USA 88, 7496–7499.
Rost et al., (1995) Protein Science 4, 521–533.
Sambrook et al., (1989) Molecular Cloning: A Laboratory Manual, 2nd edition (Cold Spring Harbor, N.Y.: Cold Spring Harbor Laboratory Press).
Sancar, A. (1994) Biochemistry 33, 2–9.
Sander & Schneider, (1991) Proteins 9, 56–68.
Sandmann, G. (1994) Eur. J. Biochem. 223, 7–24.
Scolnik & Bartley, (1995) Plant Physiol. 108, 1342.
Siefermann-Harms, D. (1987) Physiol. Plant. 69, 561–568.
Spurgeon & Porter, (1980). Biosynthesis of carotenoids. In Biochemistry of Isoprenoid Compounds, J. W. Porter, and S. L. Spurgeon, eds. (New York: Wiley), pp. 1–122.
Tomes, M. L. (1963) Bot. Gaz. 124, 180–185.
Tomes, M. L. (1967) Genetics 56, 227–232.
Tuveson et al., (1986) J. Bacteriol. 170, 4675–4680.
Van Beeumen et al., (1991) J. Biol. Chem. 266, 12921–12931.
Weedon & Moss, (1995) Structure and Nomenclature. In Carotenoids, Vol. IB: Spectroscopy, G. Britton, S. Liaaen-Jensen, H. P. Pfander, eds. (Basel: Birkhauser Verlag), pp. 27–70.
Wierenga et al., (1986) J. Mol. Biol. 187, 101–107.
Zechmeister, L. (1962) Cis-Trans Isomeric Carotenoids, Vitamins A and Arylpolyenes. Springer-Verlag, Vienna.

Having now fully described the invention, it will be apparent to one of ordinary skill in the art that many changes and modifications can be made thereto without departing from the spirit or scope of the invention as set forth herein.

What is claimed as new and is desired to be secured by letters patent of the United States is:

1. An isolated eukaryotic enzyme which is a ε cyclase enzyme having the amino acid sequence of SEQ ID NO: 2.
2. An isolated DNA sequence comprising a gene encoding the eukaryotic ε cyclase of claim 1.
3. The isolated DNA sequence according to claim 2, having the nucleic acid sequence of SEQ ID NO: 1.
4. An expression vector comprising the DNA sequence of claim 2.
5. A host cell containing the expression vector of claim 4.
6. The expression vector according to claim 4 which is pATeps deposited with the American Type Culture Collection on Mar. 4, 1996 under accession number 98005.
7. A host cell containing the expression vector of claim 6.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
    ( A ) LENGTH: 1860 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS (B) LOCATION: 109..1680
(D) OTHER INFORMATION: /product="E-CYCLASE FROM A. THALIANA"

(xi) SEQUENCE DESCRIPTION: SEQ ID NO:1:

```
ACAAAAGGAA ATAATTAGAT TCCTCTTTCT GCTTGCTATA CCTTGATAGA ACAATATAAC        60

AATGGTGTAA GTCTTCTCGC TGTATTCGAA ATTATTTGGA GGAGGAAA ATG GAG TGT       117
                                                      Met Glu Cys
                                                        1

GTT GGG GCT AGG AAT TTC GCA GCA ATG GCG GTT TCA ACA TTT CCG TCA        165
Val Gly Ala Arg Asn Phe Ala Ala Met Ala Val Ser Thr Phe Pro Ser
      5               10                  15

TGG AGT TGT CGA AGG AAA TTT CCA GTG GTT AAG AGA TAC AGC TAT AGG        213
Trp Ser Cys Arg Arg Lys Phe Pro Val Val Lys Arg Tyr Ser Tyr Arg
 20              25                  30                      35

AAT ATT CGT TTC GGT TTG TGT AGT GTC AGA GCT AGC GGC GGA AGT            261
Asn Ile Arg Phe Gly Leu Cys Ser Val Arg Ala Ser Gly Gly Gly Ser
                  40                  45                  50

TCC GGT AGT GAG AGT TGT GTA GCG GTG AGA GAA GAT TTC GCT GAC GAA        309
Ser Gly Ser Glu Ser Cys Val Ala Val Arg Glu Asp Phe Ala Asp Glu
              55                  60                  65

GAA GAT TTT GTG AAA GCT GGT GGT TCT GAG ATT CTA TTT GTT CAA ATG        357
Glu Asp Phe Val Lys Ala Gly Gly Ser Glu Ile Leu Phe Val Gln Met
          70                  75                  80

CAG CAG AAC AAA GAT ATG GAT GAA CAG TCT AAG CTT GTT GAT AAG TTG        405
Gln Gln Asn Lys Asp Met Asp Glu Gln Ser Lys Leu Val Asp Lys Leu
      85                  90                  95

CCT CCT ATA TCA ATT GGT GAT GGT GCT TTG GAT CAT GTG GTT ATT GGT        453
Pro Pro Ile Ser Ile Gly Asp Gly Ala Leu Asp His Val Val Ile Gly
100              105                 110                 115

TGT GGT CCT GCT GGT TTA GCC TTG GCT GCA GAA TCA GCT AAG CTT GGA        501
Cys Gly Pro Ala Gly Leu Ala Leu Ala Ala Glu Ser Ala Lys Leu Gly
                  120                 125                 130

TTA AAA GTT GGA CTC ATT GGT CCA GAT CTT CCT TTT ACT AAC AAT TAC        549
Leu Lys Val Gly Leu Ile Gly Pro Asp Leu Pro Phe Thr Asn Asn Tyr
              135                 140                 145

GGT GTT TGG GAA GAT GAA TTC AAT GAT CTT GGG CTG CAA AAA TGT ATT        597
Gly Val Trp Glu Asp Glu Phe Asn Asp Leu Gly Leu Gln Lys Cys Ile
          150                 155                 160

GAG CAT GTT TGG AGA GAG ACT ATT GTG TAT CTG GAT GAT GAC AAG CCT        645
Glu His Val Trp Arg Glu Thr Ile Val Tyr Leu Asp Asp Asp Lys Pro
    165                 170                 175

ATT ACC ATT GGC CGT GCT TAT GGA AGA GTT AGT CGA CGT TTG CTC CAT        693
Ile Thr Ile Gly Arg Ala Tyr Gly Arg Val Ser Arg Arg Leu Leu His
180              185                 190                 195

GAG GAG CTT TTG AGG AGG TGT GTC GAG TCA GGT GTC TCG TAC CTT AGC        741
Glu Glu Leu Leu Arg Arg Cys Val Glu Ser Gly Val Ser Tyr Leu Ser
                  200                 205                 210

TCG AAA GTT GAC AGC ATA ACA GAA GCT TCT GAT GGC CTT AGA CTT GTT        789
Ser Lys Val Asp Ser Ile Thr Glu Ala Ser Asp Gly Leu Arg Leu Val
              215                 220                 225

GCT TGT GAC GAC AAT AAC GTC ATT CCC TGC AGG CTT GCC ACT GTT GCT        837
Ala Cys Asp Asp Asn Asn Val Ile Pro Cys Arg Leu Ala Thr Val Ala
          230                 235                 240

TCT GGA GCA GCT TCG GGA AAG CTC TTG CAA TAC GAA GTT GGT GGA CCT        885
Ser Gly Ala Ala Ser Gly Lys Leu Leu Gln Tyr Glu Val Gly Gly Pro
    245                 250                 255

AGA GTC TGT GTG CAA ACT GCA TAC GGC GTG GAG GTT GAG GTG GAA AAT        933
Arg Val Cys Val Gln Thr Ala Tyr Gly Val Glu Val Glu Val Glu Asn
260              265                 270                 275
```

-continued

| | | | | | | | | | | | | | | | | |
|---|---|---|---|---|---|---|---|---|---|---|---|---|---|---|---|---|
| AGT | CCA | TAT | GAT | CCA | GAT | CAA | ATG | GTT | TTC | ATG | GAT | TAC | AGA | GAT | TAT | 981 |
| Ser | Pro | Tyr | Asp 280 | Pro | Asp | Gln | Met | Val | Phe 285 | Met | Asp | Tyr | Arg | Asp 290 | Tyr | |
| ACT | AAC | GAG | AAA | GTT | CGG | AGC | TTA | GAA | GCT | GAG | TAT | CCA | ACG | TTT | CTG | 1029 |
| Thr | Asn | Glu | Lys 295 | Val | Arg | Ser | Leu | Glu 300 | Ala | Glu | Tyr | Pro | Thr 305 | Phe | Leu | |
| TAC | GCC | ATG | CCT | ATG | ACA | AAG | TCA | AGA | CTC | TTC | TTC | GAG | GAG | ACA | TGT | 1077 |
| Tyr | Ala | Met 310 | Pro | Met | Thr | Lys | Ser 315 | Arg | Leu | Phe | Phe | Glu 320 | Glu | Thr | Cys | |
| TTG | GCC | TCA | AAA | GAT | GTC | ATG | CCC | TTT | GAT | TTG | CTA | AAA | ACG | AAG | CTC | 1125 |
| Leu | Ala 325 | Ser | Lys | Asp | Val | Met 330 | Pro | Phe | Asp | Leu | Leu 335 | Lys | Thr | Lys | Leu | |
| ATG | TTA | AGA | TTA | GAT | ACA | CTC | GGA | ATT | CGA | ATT | CTA | AAG | ACT | TAC | GAA | 1173 |
| Met 340 | Leu | Arg | Leu | Asp | Thr 345 | Leu | Gly | Ile | Arg | Ile 350 | Leu | Lys | Thr | Tyr | Glu 355 | |
| GAG | GAG | TGG | TCC | TAT | ATC | CCA | GTT | GGT | GGT | TCC | TTG | CCA | AAC | ACC | GAA | 1221 |
| Glu | Glu | Trp | Ser | Tyr 360 | Ile | Pro | Val | Gly | Gly 365 | Ser | Leu | Pro | Asn | Thr 370 | Glu | |
| CAA | AAG | AAT | CTC | GCC | TTT | GGT | GCT | GCC | GCT | AGC | ATG | GTA | CAT | CCC | GCA | 1269 |
| Gln | Lys | Asn | Leu 375 | Ala | Phe | Gly | Ala | Ala 380 | Ala | Ser | Met | Val | His 385 | Pro | Ala | |
| ACA | GGC | TAT | TCA | GTT | GTG | AGA | TCT | TTG | TCT | GAA | GCT | CCA | AAA | TAT | GCA | 1317 |
| Thr | Gly | Tyr 390 | Ser | Val | Val | Arg | Ser 395 | Leu | Ser | Glu | Ala | Pro 400 | Lys | Tyr | Ala | |
| TCA | GTC | ATC | GCA | GAG | ATA | CTA | AGA | GAA | GAG | ACT | ACC | AAA | CAG | ATC | AAC | 1365 |
| Ser | Val 405 | Ile | Ala | Glu | Ile | Leu 410 | Arg | Glu | Glu | Thr | Thr 415 | Lys | Gln | Ile | Asn | |
| AGT | AAT | ATT | TCA | AGA | CAA | GCT | TGG | GAT | ACT | TTA | TGG | CCA | CCA | GAA | AGG | 1413 |
| Ser 420 | Asn | Ile | Ser | Arg | Gln 425 | Ala | Trp | Asp | Thr | Leu 430 | Trp | Pro | Pro | Glu | Arg 435 | |
| AAA | AGA | CAG | AGA | GCA | TTC | TTT | CTC | TTT | GGT | CTT | GCA | CTC | ATA | GTT | CAA | 1461 |
| Lys | Arg | Gln | Arg | Ala 440 | Phe | Phe | Leu | Phe | Gly 445 | Leu | Ala | Leu | Ile | Val 450 | Gln | |
| TTC | GAT | ACC | GAA | GGC | ATT | AGA | AGC | TTC | TTC | CGT | ACT | TTC | TTC | CGC | CTT | 1509 |
| Phe | Asp | Thr | Glu 455 | Gly | Ile | Arg | Ser | Phe 460 | Phe | Arg | Thr | Phe | Phe 465 | Arg | Leu | |
| CCA | AAA | TGG | ATG | TGG | CAA | GGG | TTT | CTA | GGA | TCA | ACA | TTA | ACA | TCA | GGA | 1557 |
| Pro | Lys | Trp 470 | Met | Trp | Gln | Gly | Phe 475 | Leu | Gly | Ser | Thr | Leu 480 | Thr | Ser | Gly | |
| GAT | CTC | GTT | CTC | TTT | GCT | TTA | TAC | ATG | TTC | GTC | ATT | TCA | CCA | AAC | AAT | 1605 |
| Asp | Leu | Val 485 | Leu | Phe | Ala | Leu | Tyr 490 | Met | Phe | Val | Ile | Ser 495 | Pro | Asn | Asn | |
| TTG | AGA | AAA | GGT | CTC | ATC | AAT | CAT | CTC | ATC | TCT | GAT | CCA | ACC | GGA | GCA | 1653 |
| Leu | Arg | Lys | Gly 500 | Leu | Ile | Asn | His 505 | Leu | Ile | Ser | Asp | Pro 510 | Thr | Gly | Ala 515 | |
| ACC | ATG | ATA | AAA | ACC | TAT | CTC | AAA | GTA | TGATTTACTT | | | ATCAACTCTT | | | | 1700 |
| Thr | Met | Ile | Lys | Thr 520 | Tyr | Leu | Lys | Val | | | | | | | | |

AGGTTTGTGT ATATATATGT TGATTTATCT GAATAATCGA TCAAAGAATG GTATGTGGGT  1760

TACTAGGAAG TTGGAAACAA ACATGTATAG AATCTAAGGA GTGATCGAAA TGGAGATGGA  1820

AACGAAAAGA AAAAAATCAG TCTTTGTTTT GTGGTTAGTG  1860

( 2 ) INFORMATION FOR SEQ ID NO:2:

( i ) SEQUENCE CHARACTERISTICS:
    ( A ) LENGTH: 524 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| Met 1 | Glu | Cys | Val | Gly 5 | Ala | Arg | Asn | Phe | Ala 10 | Ala | Met | Ala | Val | Ser 15 | Thr |
|---|---|---|---|---|---|---|---|---|---|---|---|---|---|---|---|
| Phe | Pro | Ser | Trp 20 | Ser | Cys | Arg | Arg | Lys 25 | Phe | Pro | Val | Val | Lys 30 | Arg | Tyr |
| Ser | Tyr | Arg 35 | Asn | Ile | Arg | Phe | Gly 40 | Leu | Cys | Ser | Val | Arg 45 | Ala | Ser | Gly |
| Gly | Gly 50 | Ser | Ser | Gly | Ser | Glu 55 | Ser | Cys | Val | Ala | Val 60 | Arg | Glu | Asp | Phe |
| Ala 65 | Asp | Glu | Glu | Asp | Phe 70 | Val | Lys | Ala | Gly | Gly 75 | Ser | Glu | Ile | Leu | Phe 80 |
| Val | Gln | Met | Gln | Gln 85 | Asn | Lys | Asp | Met | Asp 90 | Glu | Gln | Ser | Lys | Leu 95 | Val |
| Asp | Lys | Leu | Pro 100 | Pro | Ile | Ser | Ile | Gly 105 | Asp | Gly | Ala | Leu | Asp 110 | His | Val |
| Val | Ile | Gly 115 | Cys | Gly | Pro | Ala | Gly 120 | Leu | Ala | Leu | Ala | Ala 125 | Glu | Ser | Ala |
| Lys | Leu 130 | Gly | Leu | Lys | Val | Gly 135 | Leu | Ile | Gly | Pro | Asp 140 | Leu | Pro | Phe | Thr |
| Asn 145 | Asn | Tyr | Gly | Val | Trp 150 | Glu | Asp | Glu | Phe | Asn 155 | Asp | Leu | Gly | Leu | Gln 160 |
| Lys | Cys | Ile | Glu | His 165 | Val | Trp | Arg | Glu | Thr 170 | Ile | Val | Tyr | Leu | Asp 175 | Asp |
| Asp | Lys | Pro | Ile 180 | Thr | Ile | Gly | Arg | Ala 185 | Tyr | Gly | Arg | Val | Ser 190 | Arg | Arg |
| Leu | Leu | His 195 | Glu | Glu | Leu | Leu | Arg 200 | Arg | Cys | Val | Glu | Ser 205 | Gly | Val | Ser |
| Tyr | Leu 210 | Ser | Ser | Lys | Val | Asp 215 | Ser | Ile | Thr | Glu | Ala 220 | Ser | Asp | Gly | Leu |
| Arg 225 | Leu | Val | Ala | Cys | Asp 230 | Asp | Asn | Asn | Val | Ile 235 | Pro | Cys | Arg | Leu | Ala 240 |
| Thr | Val | Ala | Ser | Gly 245 | Ala | Ala | Ser | Gly | Lys 250 | Leu | Leu | Gln | Tyr | Glu 255 | Val |
| Gly | Gly | Pro | Arg 260 | Val | Cys | Val | Gln | Thr 265 | Ala | Tyr | Gly | Val | Glu 270 | Val | Glu |
| Val | Glu | Asn 275 | Ser | Pro | Tyr | Asp | Pro 280 | Asp | Gln | Met | Val | Phe 285 | Met | Asp | Tyr |
| Arg | Asp 290 | Tyr | Thr | Asn | Glu | Lys 295 | Val | Arg | Ser | Leu | Glu 300 | Ala | Glu | Tyr | Pro |
| Thr 305 | Phe | Leu | Tyr | Ala | Met 310 | Pro | Met | Thr | Lys | Ser 315 | Arg | Leu | Phe | Phe | Glu 320 |
| Glu | Thr | Cys | Leu | Ala 325 | Ser | Lys | Asp | Val | Met 330 | Pro | Phe | Asp | Leu | Leu 335 | Lys |
| Thr | Lys | Leu | Met 340 | Leu | Arg | Leu | Asp | Thr 345 | Leu | Gly | Ile | Arg | Ile 350 | Leu | Lys |
| Thr | Tyr | Glu 355 | Glu | Glu | Trp | Ser | Tyr 360 | Ile | Pro | Val | Gly | Gly 365 | Ser | Leu | Pro |
| Asn | Thr 370 | Glu | Gln | Lys | Asn | Leu 375 | Ala | Phe | Gly | Ala | Ala 380 | Ala | Ser | Met | Val |
| His 385 | Pro | Ala | Thr | Gly | Tyr 390 | Ser | Val | Val | Arg | Ser 395 | Leu | Ser | Glu | Ala | Pro 400 |
| Lys | Tyr | Ala | Ser | Val 405 | Ile | Ala | Glu | Ile | Leu 410 | Arg | Glu | Glu | Thr | Lys 415 |  |

-continued

| Gln | Ile | Asn | Ser | Asn | Ile | Ser | Arg | Gln | Ala | Trp | Asp | Thr | Leu | Trp | Pro |
| | | | 420 | | | | 425 | | | | | 430 | | | |

| Pro | Glu | Arg | Lys | Arg | Gln | Arg | Ala | Phe | Phe | Leu | Phe | Gly | Leu | Ala | Leu |
| | | 435 | | | | 440 | | | | | 445 | | | | |

| Ile | Val | Gln | Phe | Asp | Thr | Glu | Gly | Ile | Arg | Ser | Phe | Phe | Arg | Thr | Phe |
| | 450 | | | | 455 | | | | | 460 | | | | | |

| Phe | Arg | Leu | Pro | Lys | Trp | Met | Trp | Gln | Gly | Phe | Leu | Gly | Ser | Thr | Leu |
| 465 | | | | | 470 | | | | 475 | | | | | | 480 |

| Thr | Ser | Gly | Asp | Leu | Val | Leu | Phe | Ala | Leu | Tyr | Met | Phe | Val | Ile | Ser |
| | | | 485 | | | | | 490 | | | | 495 | | | |

| Pro | Asn | Asn | Leu | Arg | Lys | Gly | Leu | Ile | Asn | His | Leu | Ile | Ser | Asp | Pro |
| | | 500 | | | | | 505 | | | | | 510 | | | |

| Thr | Gly | Ala | Thr | Met | Ile | Lys | Thr | Tyr | Leu | Lys | Val |
| | | 515 | | | | | 520 | | | | |

( 2 ) INFORMATION FOR SEQ ID NO:3:

( i ) SEQUENCE CHARACTERISTICS:
        ( A ) LENGTH: 956 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GCTCTTTCTC CTCCTCCTCT ACCGATTTCC GACTCCGCCT CCCGAAATCC TTATCCGGAT      60
TCTCTCCGTC TCTTCGATTT AAACGCTTTT CTGTCTGTTA CGTCGTCGAA GAACGGAGAC     120
AGAATTCTCC GATTGAGAAC GATGAGAGAC CGGAGAGCAC GAGCTCCACA AACGCTATAG     180
ACGCTGAGTA TCTGGCGTTG CGTTTGGCGG AGAAATTGGA GAGGAAGAAA TCGGAGAGGT     240
CCACTTATCT AATCGCTGCT ATGTTGTCGA GCTTTGGTAT CACTTCTATG GCTGTTATGG     300
CTGTTTACTA CAGATTCTCT TGGCAAATGG AGGGAGGTGA GATCTCAATG TTGGAAATGT     360
TTGGTACATT TGCTCTCTCT GTTGGTGCTG CTGTTGGTAT GGAATTCTGG GCAAGATGGG     420
CTCATAGAGC TCTGTGGCAC GCTTCTCTAT GGAATATGCA TGAGTCACAT CACAAACCAA     480
GAGAAGGACC GTTGAGCTA AACGATGTTT TGCTATAGT GAACGCTGGT CCAGCGATTG      540
GTCTCCTCTC TTATGGATTC TTCAATAAAG GACTCGTTCC TGGTCTCTGC TTTGGCGCCG     600
GGTTAGGCAT AACGGTGTTT GGAATCGCCT ACATGTTTGT CCACGATGGT CTCGTGCACA     660
AGCGTTTCCC TGTAGGTCCC ATCGCCGACG TCCCTTACCT CCGAAAGGTC GCCGCCGCTC     720
ACCAGCTACA TCACACAGAC AAGTTCAATG GTGTACCATA TGGACTGTTT CTTGGACCCA     780
AGGAATTGGA AGAAGTTGGA GGAAATGAAG AGTTAGATAA GGAGATTAGT CGGAGAATCA     840
AATCATACAA AAAGGCCTCG GGCTCCGGGT CGAGTTCGAG TTCTTGACTT TAAACAAGTT     900
TTAAATCCCA AATTCTTTTT TTGTCTTCTG TCATTATGAT CATCTTAAGA CGGTCT        956
```

( 2 ) INFORMATION FOR SEQ ID NO:4:

( i ) SEQUENCE CHARACTERISTICS:
        ( A ) LENGTH: 294 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

| Ser | Phe | Ser | Ser | Ser | Ser | Thr | Asp | Phe | Arg | Leu | Arg | Leu | Pro | Lys | Ser |

|   |     |     |     | 5   |     |     |     |     | 10  |     |     |     |     | 15  |
|---|-----|-----|-----|-----|-----|-----|-----|-----|-----|-----|-----|-----|-----|-----|
|   | Leu | Ser | Gly | Phe | Ser | Pro | Ser | Leu | Arg | Phe | Lys | Arg | Phe | Ser | Val | Cys |
|   |     |     | 20  |     |     |     |     | 25  |     |     |     | 30  |     |     |
|   | Tyr | Val | Val | Glu | Glu | Arg | Arg | Gln | Asn | Ser | Pro | Ile | Glu | Asn | Asp | Glu |
|   |     |     | 35  |     |     |     | 40  |     |     |     |     | 45  |     |     |
|   | Arg | Pro | Glu | Ser | Thr | Ser | Ser | Thr | Asn | Ala | Ile | Asp | Ala | Glu | Tyr | Leu |
|   |     | 50  |     |     |     |     | 55  |     |     |     | 60  |     |     |     |
|   | Ala | Leu | Arg | Leu | Ala | Glu | Lys | Leu | Glu | Arg | Lys | Lys | Ser | Glu | Arg | Ser |
|   | 65  |     |     |     |     | 70  |     |     |     |     | 75  |     |     |     |     | 80  |
|   | Thr | Tyr | Leu | Ile | Ala | Ala | Met | Leu | Ser | Ser | Phe | Gly | Ile | Thr | Ser | Met |
|   |     |     |     |     | 85  |     |     |     |     | 90  |     |     |     |     | 95  |
|   | Ala | Val | Met | Ala | Val | Tyr | Tyr | Arg | Phe | Ser | Trp | Gln | Met | Glu | Gly | Gly |
|   |     |     |     | 100 |     |     |     |     | 105 |     |     |     | 110 |     |     |
|   | Glu | Ile | Ser | Met | Leu | Glu | Met | Phe | Gly | Thr | Phe | Ala | Leu | Ser | Val | Gly |
|   |     |     | 115 |     |     |     |     | 120 |     |     |     |     | 125 |     |     |
|   | Ala | Ala | Val | Gly | Met | Glu | Phe | Trp | Ala | Arg | Trp | Ala | His | Arg | Ala | Leu |
|   |     |     | 130 |     |     |     |     | 135 |     |     |     | 140 |     |     |     |
|   | Trp | His | Ala | Ser | Leu | Trp | Met | Asn | His | Glu | Ser | His | His | Lys | Pro | Arg |
|   | 145 |     |     |     |     | 150 |     |     |     |     | 155 |     |     |     |     | 160 |
|   | Glu | Gly | Pro | Phe | Glu | Leu | Asn | Asp | Val | Phe | Ala | Ile | Val | Asn | Ala | Gly |
|   |     |     |     |     | 165 |     |     |     |     | 170 |     |     |     |     | 175 |
|   | Pro | Ala | Ile | Gly | Leu | Leu | Ser | Tyr | Gly | Phe | Phe | Asn | Lys | Gly | Leu | Val |
|   |     |     |     | 180 |     |     |     |     | 185 |     |     |     | 190 |     |     |
|   | Pro | Gly | Leu | Cys | Phe | Gly | Ala | Gly | Leu | Gly | Ile | Thr | Val | Phe | Gly | Ile |
|   |     |     | 195 |     |     |     |     | 200 |     |     |     |     | 205 |     |     |
|   | Ala | Tyr | Met | Phe | Val | His | Asp | Gly | Leu | Val | His | Lys | Arg | Phe | Pro | Val |
|   |     | 210 |     |     |     |     | 215 |     |     |     |     | 220 |     |     |     |
|   | Gly | Pro | Ile | Ala | Asp | Val | Pro | Tyr | Leu | Arg | Lys | Val | Ala | Ala | Ala | His |
|   | 225 |     |     |     |     | 230 |     |     |     |     | 235 |     |     |     |     | 240 |
|   | Gln | Leu | His | His | Thr | Asp | Lys | Phe | Asn | Gly | Val | Pro | Tyr | Gly | Leu | Phe |
|   |     |     |     |     | 245 |     |     |     |     | 250 |     |     |     |     | 255 |
|   | Leu | Gly | Pro | Lys | Glu | Leu | Glu | Glu | Val | Gly | Gly | Asn | Glu | Glu | Leu | Asp |
|   |     |     |     | 260 |     |     |     |     | 265 |     |     |     | 270 |     |     |
|   | Lys | Glu | Ile | Ser | Arg | Arg | Ile | Lys | Ser | Tyr | Lys | Lys | Ala | Ser | Gly | Ser |
|   |     |     | 275 |     |     |     |     | 280 |     |     |     | 285 |     |     |
|   | Gly | Ser | Ser | Ser | Ser | Ser |
|   |     | 290 |

( 2 ) INFORMATION FOR SEQ ID NO:5:

( i ) SEQUENCE CHARACTERISTICS:
        ( A ) LENGTH: 162 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

|   | Met | Thr | Gln | Phe | Leu | Ile | Val | Val | Ala | Thr | Val | Leu | Val | Met | Glu | Leu |
|   | 1   |     |     |     | 5   |     |     |     |     | 10  |     |     |     |     | 15  |
|   | Thr | Ala | Tyr | Ser | Val | His | Arg | Trp | Ile | Met | His | Gly | Pro | Leu | Gly | Trp |
|   |     |     |     | 20  |     |     |     |     | 25  |     |     |     | 30  |     |     |
|   | Gly | Trp | His | Lys | Ser | His | His | Glu | Glu | His | Asp | His | Ala | Leu | Glu | Lys |
|   |     |     |     | 35  |     |     |     |     | 40  |     |     |     | 45  |     |     |
|   | Asn | Asp | Leu | Tyr | Gly | Val | Val | Phe | Ala | Val | Leu | Ala | Thr | Ile | Leu | Phe |
|   |     |     |     | 50  |     |     |     |     | 55  |     |     |     | 60  |     |     |

```
Thr  Val  Gly  Ala  Tyr  Trp  Trp  Pro  Val  Leu  Trp  Trp  Ile  Ala  Leu  Gly
65                       70                  75                       80

Met  Thr  Val  Tyr  Gly  Leu  Ile  Tyr  Phe  Ile  Leu  His  Asp  Gly  Leu  Val
                         85                  90                       95

His  Gln  Arg  Trp  Pro  Phe  Arg  Tyr  Ile  Pro  Arg  Arg  Gly  Tyr  Phe  Arg
               100                 105                      110

Arg  Leu  Tyr  Gln  Ala  His  Arg  Leu  His  His  Ala  Val  Glu  Gly  Arg  Asp
               115                 120                      125

His  Cys  Val  Ser  Phe  Gly  Phe  Ile  Tyr  Ala  Pro  Pro  Val  Asp  Lys  Leu
     130                      135                 140

Lys  Gln  Asp  Leu  Lys  Arg  Ser  Gly  Val  Leu  Arg  Pro  Gln  Asp  Glu  Arg
145                      150                 155                           160

Pro  Ser
```

( 2 ) INFORMATION FOR SEQ ID NO:6:

( i ) SEQUENCE CHARACTERISTICS:
        ( A ) LENGTH: 175 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met  Leu  Asn  Ser  Leu  Ile  Val  Ile  Leu  Ser  Val  Ile  Ala  Met  Glu  Gly
1                        5                   10                      15

Ile  Ala  Ala  Phe  Thr  His  Arg  Tyr  Ile  Met  His  Gly  Trp  Gly  Trp  Arg
                    20                  25                       30

Trp  His  Glu  Ser  His  His  Thr  Pro  Arg  Lys  Gly  Val  Phe  Glu  Leu  Asn
          35                       40                      45

Asp  Leu  Phe  Ala  Val  Val  Phe  Ala  Gly  Val  Ala  Ile  Ala  Leu  Ile  Ala
     50                       55                  60

Val  Gly  Thr  Ala  Gly  Val  Trp  Pro  Leu  Gln  Trp  Ile  Gly  Cys  Gly  Met
65                       70                  75                       80

Thr  Val  Tyr  Gly  Leu  Leu  Tyr  Phe  Leu  Val  His  Asp  Gly  Leu  Val  His
                    85                  90                       95

Gln  Arg  Trp  Pro  Phe  His  Trp  Ile  Pro  Arg  Arg  Gly  Tyr  Leu  Lys  Arg
               100                 105                      110

Leu  Tyr  Val  Ala  His  Arg  Leu  His  His  Ala  Val  Arg  Gly  Arg  Glu  Gly
          115                 120                      125

Cys  Val  Ser  Phe  Gly  Phe  Ile  Tyr  Ala  Arg  Lys  Pro  Ala  Asp  Leu  Gln
     130                      135                 140

Ala  Ile  Leu  Arg  Glu  Arg  His  Gly  Arg  Pro  Pro  Lys  Arg  Asp  Ala  Ala
145                      150                 155                           160

Lys  Asp  Arg  Pro  Asp  Ala  Ala  Ser  Pro  Ser  Ser  Ser  Pro  Glu
               165                 170                      175
```

( 2 ) INFORMATION FOR SEQ ID NO:7:

( i ) SEQUENCE CHARACTERISTICS:
        ( A ) LENGTH: 175 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

| Met<br>1 | Leu | Trp | Ile | Trp<br>5 | Asn | Ala | Leu | Ile | Val<br>10 | Phe | Val | Thr | Val | Ile<br>15 | Gly |
|---|---|---|---|---|---|---|---|---|---|---|---|---|---|---|---|
| Met | Glu | Val | Ile<br>20 | Ala | Ala | Leu | Ala | His<br>25 | Lys | Tyr | Ile | Met | His<br>30 | Gly | Trp |
| Gly | Trp | Gly<br>35 | Trp | His | Leu | Ser | His<br>40 | His | Glu | Pro | Arg | Lys<br>45 | Gly | Ala | Phe |
| Glu | Val<br>50 | Asn | Asp | Leu | Tyr | Ala<br>55 | Val | Val | Phe | Ala | Ala<br>60 | Leu | Ser | Ile | Leu |
| Leu<br>65 | Ile | Tyr | Leu | Gly | Ser<br>70 | Thr | Gly | Met | Trp | Pro<br>75 | Leu | Gln | Trp | Ile | Gly<br>80 |
| Ala | Gly | Met | Thr | Ala<br>85 | Tyr | Gly | Leu | Leu | Tyr<br>90 | Phe | Met | Val | His | Asp<br>95 | Gly |
| Leu | Val | His | Gln<br>100 | Arg | Trp | Pro | Phe | Arg<br>105 | Tyr | Ile | Pro | Arg | Lys<br>110 | Gly | Tyr |
| Leu | Lys | Arg<br>115 | Leu | Tyr | Met | Ala | His<br>120 | Arg | Met | His | His | Ala<br>125 | Val | Arg | Gly |
| Lys | Glu<br>130 | Gly | Cys | Val | Ser | Phe<br>135 | Gly | Phe | Leu | Tyr | Ala<br>140 | Pro | Pro | Leu | Ser |
| Lys<br>145 | Leu | Gln | Ala | Thr | Leu<br>150 | Arg | Glu | Arg | His | Gly<br>155 | Ala | Arg | Ala | Gly | Ala<br>160 |
| Ala | Arg | Asp | Ala | Gln<br>165 | Gly | Gly | Glu | Asp | Glu<br>170 | Pro | Ala | Ser | Gly | Lys<br>175 | . |

( 2 ) INFORMATION FOR SEQ ID NO:8:

( i ) SEQUENCE CHARACTERISTICS:
        ( A ) LENGTH: 162 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

| Met<br>1 | Thr | Asn | Phe | Leu<br>5 | Ile | Val | Val | Ala | Thr<br>10 | Val | Leu | Val | Met | Glu<br>15 | Leu |
|---|---|---|---|---|---|---|---|---|---|---|---|---|---|---|---|
| Thr | Ala | Tyr | Ser<br>20 | Val | His | Arg | Trp | Ile<br>25 | Met | His | Gly | Pro | Leu<br>30 | Gly | Trp |
| Gly | Trp | His<br>35 | Lys | Ser | His | His | Glu<br>40 | Glu | His | Asp | His | Ala<br>45 | Leu | Glu | Lys |
| Asn | Asp<br>50 | Leu | Tyr | Gly | Leu | Val<br>55 | Phe | Ala | Val | Ile | Ala<br>60 | Thr | Val | Leu | Phe |
| Thr<br>65 | Val | Gly | Trp | Ile | Trp<br>70 | Ala | Pro | Val | Leu | Trp<br>75 | Trp | Ile | Ala | Leu | Gly<br>80 |
| Met | Thr | Val | Tyr | Gly<br>85 | Leu | Ile | Tyr | Phe | Val<br>90 | Leu | His | Asp | Gly | Leu<br>95 | Val |
| His | Trp | Arg | Trp<br>100 | Pro | Phe | Arg | Tyr | Ile<br>105 | Pro | Arg | Lys | Gly | Tyr<br>110 | Ala | Arg |
| Arg | Leu | Tyr<br>115 | Gln | Ala | His | Arg | Leu<br>120 | His | His | Ala | Val | Glu<br>125 | Gly | Arg | Asp |
| His | Cys<br>130 | Val | Ser | Phe | Gly | Phe<br>135 | Ile | Tyr | Ala | Pro | Pro<br>140 | Val | Asp | Lys | Leu |
| Lys<br>145 | Gln | Asp | Leu | Lys | Met<br>150 | Ser | Gly | Val | Leu | Arg<br>155 | Ala | Glu | Ala | Gln | Glu<br>160 |
| Arg | Thr | | | | | | | | | | | | | | |

( 2 ) INFORMATION FOR SEQ ID NO:9:

(i) SEQUENCE CHARACTERISTICS:
    (A) LENGTH: 954 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:9:

| | | | | | | |
|---|---|---|---|---|---|---|
| CCACGGGTCC | GCCTCCCCGT | TTTTTCCGA | TCCGATCTCC | GGTGCCGAGG | ACTCAGCTGT | 60 |
| TTGTTCGCGC | TTTCTCAGCC | GTCACCATGA | CCGATTCTAA | CGATGCTGGA | ATGGATGCTG | 120 |
| TTCAGAGACG | ACTCATGTTT | GAAGACGAAT | GCATTCTCGT | TGATGAAAAT | AATCGTGTGG | 180 |
| TGGGACATGA | CACTAAGTAT | AACTGTCATC | TGATGGAAAA | GATTGAAGCT | GAGAATTTAC | 240 |
| TTCACAGAGC | TTTCAGTGTG | TTTTATTCA | ACTCCAAGTA | TGAGTTGCTT | CTCCAGCAAC | 300 |
| GGTCAAAAAC | AAAGGTTACT | TTCCCACTTG | TGTGGACAAA | CACTTGTTGC | AGCCATCCTC | 360 |
| TTTACCGTGA | ATCCGAGCTT | ATTGAAGAGA | ATGTGCTTGG | TGTAAGAAAT | GCCGCACAAA | 420 |
| GGAAGCTTTT | CGATGAGCTC | GGTATTGTAG | CAGAAGATGT | ACCAGTCGAT | GAGTTCACTC | 480 |
| CCTTGGGACG | CATGCTTTAC | AAGGCACCTT | CTGATGGGAA | ATGGGGAGAG | CACGAAGTTG | 540 |
| ACTATCTACT | CTTCATCGTG | CGGGATGTGA | AGCTTCAACC | AAACCCAGAT | GAAGTGGCTG | 600 |
| AGATCAAGTA | CGTGAGCAGG | GAAGAGCTTA | AGGAGCTGGT | GAAGAAAGCA | GATGCTGGCG | 660 |
| ATGAAGCTGT | GAAACTATCT | CCATGGTTCA | GATTGGTGGT | GGATAATTTC | TTGATGAAGT | 720 |
| GGTGGGATCA | TGTTGAGAAA | GGAACTATCA | CTGAAGCTGC | AGACATGAAA | ACCATTCACA | 780 |
| AGCTCTGAAC | TTTCCATAAG | TTTTGGATCT | TCCCCTTCCC | ATAATAAAAT | TAAGAGATGA | 840 |
| GACTTTTATT | GATTACAGAC | AAAACTGGCA | ACAAAATCTA | TTCCTAGGAT | TTTTTTTGC | 900 |
| TTTTTATTTA | CTTTGATTC | ATCTCTAGTT | TAGTTTCAT | CTTAAAAAAA | AAAA | 954 |

(2) INFORMATION FOR SEQ ID NO:10:

(i) SEQUENCE CHARACTERISTICS:
    (A) LENGTH: 996 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

| | | | | | | |
|---|---|---|---|---|---|---|
| CACCAATGTC | TGTTTCTTCT | TTATTTAATC | TCCCATTGAT | TCGCCTCAGA | TCTCTCGCTC | 60 |
| TTTCGTCTTC | TTTTTCTTCT | TTCCGATTTG | CCCATCGTCC | TCTGTCATCG | ATTTCACCGA | 120 |
| GAAAGTTACC | GAATTTTCGT | GCTTTCTCTG | GTACCGCTAT | GACAGATACT | AAAGATGCTG | 180 |
| GTATGGATGC | TGTTCAGAGA | CGTCTCATGT | TTGAGGATGA | ATGCATTCTT | GTTGATGAAA | 240 |
| CTGATCGTGT | TGTGGGGCAT | GTCAGCAAGT | ATAATTGTCA | TCTGATGGAA | AATATTGAAG | 300 |
| CCAAGAATTT | GCTGCACAGG | GCTTTTAGTG | TATTTTTATT | CAACTCGAAG | TATGAGTTGC | 360 |
| TTCTCCAGCA | AAGGTCAAAC | ACAAAGGTTA | CGTTCCCTCT | AGTGTGGACT | AACACTTGTT | 420 |
| GCAGCCATCC | TCTTTACCGT | GAATCAGAGC | TTATCCAGGA | CAATGCACTA | GGTGTGAGGA | 480 |
| ATGCTGCACA | AAGAAAGCTT | CTCGATGAGC | TTGGTATTGT | AGCTGAAGAT | GTACCAGTCG | 540 |
| ATGAGTTCAC | TCCCTTGGGA | CGTATGCTGT | ACAAGGCTCC | TTCTGATGGC | AAATGGGGAG | 600 |
| AGCATGAACT | TGATTACTTG | CTCTTCATCG | TGCGAGACGT | GAAGGTTCAA | CCAAACCCAG | 660 |
| ATGAAGTAGC | TGAGATCAAG | TATGTGAGCC | GGGAAGAGCT | GAAGGAGCTG | GTGAAGAAAG | 720 |

| CAGATGCAGG | TGAGGAAGGT | TTGAAACTGT | CACCATGGTT | CAGATTGGTG | GTGGACAATT | 780 |
| TCTTGATGAA | GTGGTGGGAT | CATGTTGAGA | AAGGAACTTT | GGTTGAAGCT | ATAGACATGA | 840 |
| AAACCATCCA | CAAACTCTGA | ACATCTTTTT | TTAAAGTTTT | TAAATCAATC | AACTTTCTCT | 900 |
| TCATCATTTT | TATCTTTTCG | ATGATAATAA | TTTGGGATAT | GTGAGACACT | TACAAAACTT | 960 |
| CCAAGCACCT | CAGGCAATAA | TAAAGTTTGC | GGCCGC | | | 996 |

( 2 ) INFORMATION FOR SEQ ID NO:11:

( i ) SEQUENCE CHARACTERISTICS:
        ( A ) LENGTH: 1165 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

| CTCGGTAGCT | GGCCACAATC | GCTATTTGGA | ACCTGGCCCG | GCGGCAGTCC | GATGCCGCGA | 60 |
| TGCTTCGTTC | GTTGCTCAGA | GGCCTCACGC | ATATCCCCCG | CGTGAACTCC | GCCCAGCAGC | 120 |
| CCAGCTGTGC | ACACGCGCGA | CTCCAGTTTA | AGCTCAGGAG | CATGCAGATG | ACGCTCATGC | 180 |
| AGCCCAGCAT | CTCAGCCAAT | CTGTCGCGCG | CCGAGGACCG | CACAGACCAC | ATGAGGGGTG | 240 |
| CAAGCACCTG | GGCAGGCGGG | CAGTCGCAGG | ATGAGCTGAT | GCTGAAGGAC | GAGTGCATCT | 300 |
| TGGTGGATGT | TGAGGACAAC | ATCACAGGCC | ATGCCAGCAA | GCTGGAGTGT | CACAAGTTCC | 360 |
| TACCACATCA | GCCTGCAGGC | CTGCTGCACC | GGGCCTTCTC | TGTGTTCCTG | TTTGACGATC | 420 |
| AGGGGCGACT | GCTGCTGCAA | CAGCGTGCAC | GCTCAAAAAT | CACCTTCCCA | AGTGTGTGGA | 480 |
| CGAACACCTG | CTGCAGCCAC | CCTTTACATG | GGCAGACCCC | AGATGAGGTG | GACCAACTAA | 540 |
| GCCAGGTGGC | CGACGGAACA | GTACCTGGCG | CAAAGGCTGC | TGCCATCCGC | AAGTTGGAGC | 600 |
| ACGAGCTGGG | GATACCAGCG | CACCAGCTGC | CGGCAAGCGC | GTTTCGCTTC | CTCACGCGTT | 660 |
| TGCACTACTG | TGCCGCGGAC | GTGCAGCCAG | CTGCGACACA | ATCAGCGCTC | TGGGGCGAGC | 720 |
| ACGAAATGGA | CTACATCTTG | TTCATCCGGG | CCAACGTCAC | CTTGGCGCCC | AACCCTGACG | 780 |
| AGGTGGACGA | AGTCAGGTAC | GTGACGCAAG | AGGAGCTGCG | GCAGATGATG | CAGCCGGACA | 840 |
| ACGGGCTGCA | ATGGTCGCCG | TGGTTTCGCA | TCATCGCCGC | GCGCTTCCTT | GAGCGTTGGT | 900 |
| GGGCTGACCT | GGACGCGGCC | CTAAACACTG | ACAAACACGA | GGATTGGGGA | ACGGTGCATC | 960 |
| ACATCAACGA | AGCGTGAAAG | CAGAAGCTGC | AGGATGTGAA | GACACGTCAT | GGGGTGGAAT | 1020 |
| TGCGTACTTG | GCAGCTTCGT | ATCTCCTTTT | TCTGAGACTG | AACCTGCAGT | CAGGTCCCAC | 1080 |
| AAGGTCAGGT | AAAATGGCTC | GATAAAATGT | ACCGTCACTT | TTTGTCGCGT | ATACTGAACT | 1140 |
| CCAAGAGGTC | AAAAAAAAA | AAAAA | | | | 1165 |

( 2 ) INFORMATION FOR SEQ ID NO:12:

( i ) SEQUENCE CHARACTERISTICS:
        ( A ) LENGTH: 1135 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| CTCGGTAGCT | GGCCACAATC | GCTATTTGGA | ACCTGGCCCG | GCGGCAGTCC | GATGCCGCGA | 60 |
| TGCTTCGTTC | GTTGCTCAGA | GGCCTCACGC | ATATCCCGCG | CGTGAACTCC | GCCCAGCAGC | 120 |

```
CCAGCTGTGC ACACGCGCGA CTCCAGTTTA AGCTCAGGAG CATGCAGCTG CTTTCCGAGG      180
ACCGCACAGA CCACATGAGG GGTGCAAGCA CCTGGGCAGG CGGGCAGTCG CAGGATGAGC      240
TGATGCTGAA GGACGAGTGC ATCTTGGTAG ATGTTGAGGA CAACATCACA GGCCATGCCA      300
GCAAGCTGGA GTGTCACAAG TTCCTACCAC ATCAGCCTGC AGGCCTGCTG CACCGGGCCT      360
TCTCTGTGTT CCTGTTTGAC GATCAGGGGC GACTGCTGCT GCAACAGCGT GCACGCTCAA      420
AAATCACCTT CCCAAGTGTG TGGACGAACA CCTGCTGCAG CCACCCTTTA CATGGGCAGA      480
CCCCAGATGA GGTGGACCAA CTAAGCCAGG TGGCCGACGG AACAGTACCT GGCGCAAAGG      540
CTGCTGCCAT CCGCAAGTTG GAGCACGAGC TGGGGATACC AGCGCACCAG CTGCCGGCAA      600
GCGCGTTTCG CTTCCTCACG CGTTTGCACT ACTGTGCCGC GGACGTGCAG CCAGCTGCGA      660
CACAATCAGC GCTCTGGGGC GAGCACGAAA TGGACTACAT CTTGTTCATC CGGGCCAACG      720
TCACCTTGGC GCCCAACCCT GACGAGGTGG ACGAAGTCAG GTACGTGACG CAAGAGGAGC      780
TGCGGCAGAT GATGCAGCCG GACAACGGGC TTCAATGGTC GCCGTGGTTT CGCATCATCG      840
CCGCGCGCTT CCTTGAGCGT TGGTGGGCTG ACCTGGACGC GGCCCTAAAC ACTGACAAAC      900
ACGAGGATTG GGGAACGGTG CATCACATCA CGAAGCGTG AAGGCAGAAG CTGCAGGATG       960
TGAAGACACG TCATGGGGTG GAATTGCGTA CTTGGCAGCT TCGTATCTCC TTTTTCTGAG      1020
ACTGAACCTG CAGAGCTAGA GTCAATGGTG CATCATATTC ATCGTCTCTC TTTTGTTTTA      1080
GACTAATCTG TAGCTAGAGT CACTGATGAA TCCTTTACAA CTTTCAAAAA AAAAA          1135
```

( 2 ) INFORMATION FOR SEQ ID NO:13:

( i ) SEQUENCE CHARACTERISTICS:
( A ) LENGTH: 960 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

```
CCAAAAACAA CTCAAATCTC CTCCGTCGCT CTTACTCCGC CATGGGTGAC GACTCCGGCA       60
TGGATGCTGT TCAGCGACGT CTCATGTTTG ACGATGAATG CATTTGGTG GATGAGTGTG       120
ACAATGTGGT GGGACATGAT ACCAAATACA ATTGTCACTT GATGGAGAAG ATTGAAACAG      180
GTAAAATGCT GCACAGAGCA TTCAGCGTTT TTCTATTCAA TTCAAAATAC GAGTTACTTC      240
TTCAGCAACG GTCTGCAACC AAGGTGACAT TTCCTTTAGT ATGGACCAAC ACCTGTTGCA      300
GCCATCCACT CTACAGAGAA TCCGAGCTTG TTCCCGAAAC GCCTGAGAGA ATGCTGCACA      360
GAGGANNNNN NNNNNNNNNN NNNNNNNNNN NNNNNNNNNN NNNNNNNNNN NNNNNNNNNN      420
NNNNNNNNNN NNNNNNNNNN NNNNNNNNNN NNNNNNNNNN NNNNNNNNNN NNNNNNNNNN      480
NNNNNNNNNN NNNNNNNNNN NNNNNNNNNN NNNNNNNNNN NNNNNNNNNN NNNNNNNNNN      540
NNNNNNNNNN NNNNNNNNNN NNNNNNNNNN NNNNNNNNNN NNNNNNNNNN NNNNNNNNNN      600
NNNNNNNNNN NNNNNNNNNN NNNNNNNNNN NNNNNNNNNN NNNNNNNNNN NNNNNNNNNN      660
NNNNNNNNNN NNNNNNNNNN TCATGTGCAA AAGGGTACAC TCACTGAATG CAATTTGATA      720
TGAAAACCAT ACACAAGCTG ATATAGAAAC ACACCCTCAA CCGAAAAGCA AGCCTAATAA      780
TTCGGGTTGG GTCGGGTCTA CCATCAATTG TTTTTTTCTT TTAACAACTT TTAATCTCTA      840
TTTGAGCATG TTGATTCTTG TCTTTTGTGT GTAAGATTTT GGGTTTCGTT TCAGTTGTAA      900
TAATGAACCA TTGATGGTTT GCAATTTCAA GTTCCTATCG ACATGTAGTG ATCTAAAAAA      960
```

( 2 ) INFORMATION FOR SEQ ID NO:14:

( i ) SEQUENCE CHARACTERISTICS:
        ( A ) LENGTH: 305 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Met  Leu  Arg  Ser  Leu  Leu  Arg  Gly  Leu  Thr  His  Ile  Pro  Arg  Val  Asn
 1                  5                        10                       15

Ser  Ala  Gln  Gln  Pro  Ser  Cys  Ala  His  Ala  Arg  Leu  Gln  Phe  Lys  Leu
               20                       25                       30

Arg  Ser  Met  Gln  Met  Thr  Leu  Met  Gln  Pro  Ser  Ile  Ser  Ala  Asn  Leu
          35                        40                       45

Ser  Arg  Ala  Glu  Asp  Arg  Thr  Asp  His  Met  Arg  Gly  Ala  Ser  Thr  Trp
     50                       55                       60

Ala  Gly  Gly  Gln  Ser  Gln  Asp  Glu  Leu  Met  Leu  Lys  Asp  Glu  Cys  Ile
65                       70                       75                        80

Leu  Val  Asp  Val  Glu  Asp  Asn  Ile  Thr  Gly  His  Ala  Ser  Lys  Leu  Glu
               85                       90                       95

Cys  His  Lys  Phe  Leu  Pro  His  Gln  Pro  Ala  Gly  Leu  Leu  His  Arg  Ala
               100                      105                      110

Phe  Ser  Val  Phe  Leu  Phe  Asp  Asp  Gln  Gly  Arg  Leu  Leu  Leu  Gln  Gln
               115                      120                      125

Arg  Ala  Arg  Ser  Lys  Ile  Thr  Phe  Pro  Ser  Val  Trp  Thr  Asn  Thr  Cys
     130                      135                      140

Cys  Ser  His  Pro  Leu  His  Gly  Gln  Thr  Pro  Asp  Glu  Val  Asp  Gln  Leu
145                      150                      155                      160

Ser  Gln  Val  Ala  Asp  Gly  Thr  Val  Pro  Gly  Ala  Lys  Ala  Ala  Ala  Ile
               165                      170                      175

Arg  Lys  Leu  Glu  His  Glu  Leu  Gly  Ile  Pro  Ala  His  Gln  Leu  Pro  Ala
     180                      185                      190

Ser  Ala  Phe  Arg  Phe  Leu  Thr  Arg  Leu  His  Tyr  Cys  Ala  Ala  Asp  Val
          195                      200                      205

Gln  Pro  Ala  Ala  Thr  Gln  Ser  Ala  Leu  Trp  Gly  Glu  His  Glu  Met  Asp
     210                      215                      220

Tyr  Ile  Leu  Phe  Ile  Arg  Ala  Asn  Val  Thr  Leu  Ala  Pro  Asn  Pro  Asp
225                      230                      235                      240

Glu  Val  Asp  Glu  Val  Arg  Tyr  Val  Thr  Gln  Glu  Leu  Arg  Gln  Met
               245                      250                      255

Met  Gln  Pro  Asp  Asn  Gly  Leu  Gln  Trp  Ser  Pro  Trp  Phe  Arg  Ile  Ile
          260                      265                      270

Ala  Ala  Arg  Phe  Leu  Glu  Arg  Trp  Trp  Ala  Asp  Leu  Asp  Ala  Ala  Leu
          275                      280                      285

Asn  Thr  Asp  Lys  His  Glu  Asp  Trp  Gly  Thr  Val  His  His  Ile  Asn  Glu
     290                      295                      300

Ala
305
```

( 2 ) INFORMATION FOR SEQ ID NO:15:

( i ) SEQUENCE CHARACTERISTICS:
        ( A ) LENGTH: 293 amino acids
        ( B ) TYPE: amino acid
        ( C ) STRANDEDNESS: single (D) TOPOLOGY: linear (ii) MOLECULE TYPE: protein (xi) SEQUENCE DESCRIPTION: SEQ ID NO:15:

| Met | Leu | Arg | Ser | Leu | Leu | Arg | Gly | Leu | Thr | His | Ile | Pro | Arg | Val | Asn |
|---|---|---|---|---|---|---|---|---|---|---|---|---|---|---|---|
| 1 | | | | 5 | | | | | 10 | | | | | 15 | |

| Ser | Ala | Gln | Gln | Pro | Ser | Cys | Ala | His | Ala | Arg | Leu | Gln | Phe | Lys | Leu |
|---|---|---|---|---|---|---|---|---|---|---|---|---|---|---|---|
| | | | 20 | | | | | 25 | | | | | 30 | | |

| Arg | Ser | Met | Gln | Leu | Leu | Ser | Glu | Asp | Arg | Thr | Asp | His | Met | Arg | Gly |
|---|---|---|---|---|---|---|---|---|---|---|---|---|---|---|---|
| | | | 35 | | | | | 40 | | | | | 45 | | |

| Ala | Ser | Thr | Trp | Ala | Gly | Gly | Gln | Ser | Gln | Asp | Glu | Leu | Met | Leu | Lys |
|---|---|---|---|---|---|---|---|---|---|---|---|---|---|---|---|
| | 50 | | | | | 55 | | | | | 60 | | | | |

| Asp | Glu | Cys | Ile | Leu | Val | Asp | Val | Glu | Asp | Asn | Ile | Thr | Gly | His | Ala |
|---|---|---|---|---|---|---|---|---|---|---|---|---|---|---|---|
| 65 | | | | | 70 | | | | | 75 | | | | | 80 |

| Ser | Lys | Leu | Glu | Cys | His | Lys | Phe | Leu | Pro | His | Gln | Pro | Ala | Gly | Leu |
|---|---|---|---|---|---|---|---|---|---|---|---|---|---|---|---|
| | | | | 85 | | | | | 90 | | | | | 95 | |

| Leu | His | Arg | Ala | Phe | Ser | Val | Phe | Leu | Phe | Asp | Asp | Gln | Gly | Arg | Leu |
|---|---|---|---|---|---|---|---|---|---|---|---|---|---|---|---|
| | | | 100 | | | | | 105 | | | | | 110 | | |

| Leu | Leu | Gln | Gln | Arg | Ala | Arg | Ser | Lys | Ile | Thr | Phe | Pro | Ser | Val | Trp |
|---|---|---|---|---|---|---|---|---|---|---|---|---|---|---|---|
| | | 115 | | | | | 120 | | | | | 125 | | | |

| Thr | Asn | Thr | Cys | Cys | Ser | His | Pro | Leu | His | Gly | Gln | Thr | Pro | Asp | Glu |
|---|---|---|---|---|---|---|---|---|---|---|---|---|---|---|---|
| | 130 | | | | | 135 | | | | | 140 | | | | |

| Val | Asp | Gln | Leu | Ser | Gln | Val | Ala | Asp | Gly | Thr | Val | Pro | Gly | Ala | Lys |
|---|---|---|---|---|---|---|---|---|---|---|---|---|---|---|---|
| 145 | | | | | 150 | | | | | 155 | | | | | 160 |

| Ala | Ala | Ala | Ile | Arg | Lys | Leu | Glu | His | Glu | Leu | Gly | Ile | Pro | Ala | His |
|---|---|---|---|---|---|---|---|---|---|---|---|---|---|---|---|
| | | | | 165 | | | | | 170 | | | | | 175 | |

| Gln | Leu | Pro | Ala | Ser | Ala | Phe | Arg | Phe | Leu | Thr | Arg | Leu | His | Tyr | Cys |
|---|---|---|---|---|---|---|---|---|---|---|---|---|---|---|---|
| | | | 180 | | | | | 185 | | | | | 190 | | |

| Ala | Ala | Asp | Val | Gln | Pro | Ala | Ala | Thr | Gln | Ser | Ala | Leu | Trp | Gly | Glu |
|---|---|---|---|---|---|---|---|---|---|---|---|---|---|---|---|
| | | 195 | | | | | 200 | | | | | 205 | | | |

| His | Glu | Met | Asp | Tyr | Ile | Leu | Phe | Ile | Arg | Ala | Asn | Val | Thr | Leu | Ala |
|---|---|---|---|---|---|---|---|---|---|---|---|---|---|---|---|
| | 210 | | | | | 215 | | | | | 220 | | | | |

| Pro | Asn | Pro | Asp | Glu | Val | Asp | Glu | Val | Arg | Tyr | Val | Thr | Gln | Glu | Glu |
|---|---|---|---|---|---|---|---|---|---|---|---|---|---|---|---|
| 225 | | | | | 230 | | | | | 235 | | | | | 240 |

| Leu | Arg | Gln | Met | Met | Gln | Pro | Asp | Asn | Gly | Leu | Gln | Trp | Ser | Pro | Trp |
|---|---|---|---|---|---|---|---|---|---|---|---|---|---|---|---|
| | | | | 245 | | | | | 250 | | | | | 255 | |

| Phe | Arg | Ile | Ile | Ala | Ala | Arg | Phe | Leu | Glu | Arg | Trp | Trp | Ala | Asp | Leu |
|---|---|---|---|---|---|---|---|---|---|---|---|---|---|---|---|
| | | | 260 | | | | | 265 | | | | | 270 | | |

| Asp | Ala | Ala | Leu | Asn | Thr | Asp | Lys | His | Glu | Asp | Trp | Gly | Thr | Val | His |
|---|---|---|---|---|---|---|---|---|---|---|---|---|---|---|---|
| | | 275 | | | | | 280 | | | | | 285 | | | |

| His | Ile | Asn | Glu | Ala |
|---|---|---|---|---|
| | 290 | | | |

(2) INFORMATION FOR SEQ ID NO:16:

(i) SEQUENCE CHARACTERISTICS:
  (A) LENGTH: 284 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:16:

| Met | Ser | Val | Ser | Ser | Leu | Phe | Asn | Leu | Pro | Leu | Ile | Arg | Leu | Arg | Ser |
|---|---|---|---|---|---|---|---|---|---|---|---|---|---|---|---|
| 1 | | | | 5 | | | | | 10 | | | | | 15 | |

| Leu | Ala | Leu | Ser | Ser | Ser | Phe | Ser | Ser | Phe | Arg | Phe | Ala | His | Arg | Pro |

|     |     |     |     |     | 20  |     |     |     | 25  |     |     |     | 30  |     |     |
| --- | --- | --- | --- | --- | --- | --- | --- | --- | --- | --- | --- | --- | --- | --- | --- |
| Leu | Ser | Ser<br>35 | Ile | Ser | Pro | Arg | Lys<br>40 | Leu | Pro | Asn | Phe | Arg<br>45 | Ala | Phe | Ser |
| Gly | Thr | Ala<br>50 | Met | Thr | Asp | Thr | Lys<br>55 | Asp | Ala | Gly | Met | Asp<br>60 | Ala | Val | Gln |
| Arg<br>65 | Arg | Leu | Met | Phe | Glu<br>70 | Asp | Glu | Cys | Ile | Leu<br>75 | Val | Asp | Glu | Thr | Asp<br>80 |
| Arg | Val | Val | Gly | His<br>85 | Val | Ser | Lys | Tyr | Asn<br>90 | Cys | His | Leu | Met | Glu<br>95 | Asn |
| Ile | Glu | Ala | Lys<br>100 | Asn | Leu | Leu | His | Arg<br>105 | Ala | Phe | Ser | Val | Phe<br>110 | Leu | Phe |
| Asn | Ser | Lys<br>115 | Tyr | Glu | Leu | Leu | Leu<br>120 | Gln | Gln | Arg | Ser | Asn<br>125 | Thr | Lys | Val |
| Thr | Phe<br>130 | Pro | Leu | Val | Trp | Thr<br>135 | Asn | Thr | Cys | Cys | Ser<br>140 | His | Pro | Leu | Tyr |
| Arg<br>145 | Glu | Ser | Glu | Leu | Ile<br>150 | Gln | Asp | Asn | Ala | Leu<br>155 | Gly | Val | Arg | Asn | Ala<br>160 |
| Ala | Gln | Arg | Lys | Leu<br>165 | Leu | Asp | Glu | Leu | Gly<br>170 | Ile | Val | Ala | Glu | Asp<br>175 | Val |
| Pro | Val | Asp | Glu<br>180 | Phe | Thr | Pro | Leu | Gly<br>185 | Arg | Met | Leu | Tyr | Lys<br>190 | Ala | Pro |
| Ser | Asp | Gly<br>195 | Lys | Trp | Gly | Glu | His<br>200 | Glu | Leu | Asp | Tyr | Leu<br>205 | Leu | Phe | Ile |
| Val | Arg<br>210 | Asp | Val | Lys | Val | Gln<br>215 | Pro | Asn | Pro | Asp | Glu<br>220 | Val | Ala | Glu | Ile |
| Lys<br>225 | Tyr | Val | Ser | Arg | Glu<br>230 | Glu | Leu | Lys | Glu | Leu<br>235 | Val | Lys | Lys | Ala | Asp<br>240 |
| Ala | Gly | Glu | Glu | Gly<br>245 | Leu | Lys | Leu | Ser | Pro<br>250 | Trp | Phe | Arg | Leu | Val<br>255 | Val |
| Asp | Asn | Phe | Leu<br>260 | Met | Lys | Trp | Trp | Asp<br>265 | His | Val | Glu | Lys | Gly<br>270 | Thr | Leu |
| Val | Glu | Ala<br>275 | Ile | Asp | Met | Lys | Thr<br>280 | Ile | His | Lys | Leu |     |     |     |     |

(2) INFORMATION FOR SEQ ID NO:17:

(i) SEQUENCE CHARACTERISTICS:
        (A) LENGTH: 287 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

| Met<br>1 | Ser | Ser | Ser | Met<br>5 | Leu | Asn | Phe | Thr | Ala<br>10 | Ser | Arg | Ile | Val | Ser<br>15 | Leu |
| --- | --- | --- | --- | --- | --- | --- | --- | --- | --- | --- | --- | --- | --- | --- | --- |
| Pro | Leu | Leu | Ser<br>20 | Ser | Pro | Pro | Ser | Arg<br>25 | Val | His | Leu | Pro | Leu<br>30 | Cys | Phe |
| Phe | Ser | Pro<br>35 | Ile | Ser | Leu | Thr | Gln<br>40 | Arg | Phe | Ser | Ala | Lys<br>45 | Leu | Thr | Phe |
| Ser | Ser<br>50 | Gln | Ala | Thr | Thr | Met<br>55 | Gly | Glu | Val | Val | Asp<br>60 | Ala | Gly | Met | Asp |
| Ala<br>65 | Val | Gln | Arg | Arg | Leu<br>70 | Met | Phe | Glu | Asp | Glu<br>75 | Cys | Ile | Leu | Val | Asp<br>80 |
| Glu | Asn | Asp | Lys | Val<br>85 | Val | Gly | His | Glu | Ser<br>90 | Lys | Tyr | Asn | Cys | His<br>95 | Leu |

```
Met Glu Lys Ile Glu Ser Glu Asn Leu Leu His Arg Ala Phe Ser Val
            100                 105                 110
Phe Leu Phe Asn Ser Lys Tyr Glu Leu Leu Leu Gln Gln Arg Ser Ala
        115                 120                 125
Thr Lys Val Thr Phe Pro Leu Val Trp Thr Asn Thr Cys Cys Ser His
    130                 135                 140
Pro Leu Tyr Arg Glu Ser Glu Leu Ile Asp Glu Asn Cys Leu Gly Val
145                 150                 155                 160
Arg Asn Ala Ala Gln Arg Lys Leu Leu Asp Glu Leu Gly Ile Pro Ala
                165                 170                 175
Glu Asp Leu Pro Val Asp Gln Phe Ile Pro Leu Ser Arg Ile Leu Tyr
            180                 185                 190
Lys Ala Pro Ser Asp Gly Lys Trp Gly Glu His Glu Leu Asp Tyr Leu
        195                 200                 205
Leu Phe Ile Ile Arg Asp Val Asn Leu Asp Pro Asn Pro Asp Glu Val
    210                 215                 220
Ala Glu Val Lys Tyr Met Asn Arg Asp Asp Leu Lys Glu Leu Leu Arg
225                 230                 235                 240
Lys Ala Asp Ala Glu Glu Glu Gly Val Lys Leu Ser Pro Trp Phe Arg
                245                 250                 255
Leu Val Val Asp Asn Phe Leu Phe Lys Trp Trp Asp His Val Glu Lys
            260                 265                 270
Gly Ser Leu Lys Asp Ala Ala Asp Met Lys Thr Ile His Lys Leu
        275                 280                 285
```

( 2 ) INFORMATION FOR SEQ ID NO:18:

( i ) SEQUENCE CHARACTERISTICS:
( A ) LENGTH: 261 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:18:

```
Thr Gly Pro Pro Pro Arg Phe Phe Pro Ile Arg Ser Pro Val Pro Arg
1               5                   10                  15
Thr Gln Leu Phe Val Arg Ala Phe Ser Ala Val Thr Met Thr Asp Ser
            20                  25                  30
Asn Asp Ala Gly Met Asp Ala Val Gln Arg Arg Leu Met Phe Glu Asp
        35                  40                  45
Glu Cys Ile Leu Val Asp Glu Asn Asn Arg Val Val Gly His Asp Thr
    50                  55                  60
Lys Tyr Asn Cys His Leu Met Glu Lys Ile Glu Ala Glu Asn Leu Leu
65                  70                  75                  80
His Arg Ala Phe Ser Val Phe Leu Phe Asn Ser Lys Tyr Glu Leu Leu
                85                  90                  95
Leu Gln Gln Arg Ser Lys Thr Lys Val Thr Phe Pro Leu Val Trp Thr
            100                 105                 110
Asn Thr Cys Cys Ser His Pro Leu Tyr Arg Glu Ser Glu Leu Ile Glu
        115                 120                 125
Glu Asn Val Leu Gly Val Arg Asn Ala Ala Gln Arg Lys Leu Phe Asp
    130                 135                 140
Glu Leu Gly Ile Val Ala Glu Asp Val Pro Val Asp Glu Phe Thr Pro
145                 150                 155                 160
```

```
Leu  Gly  Arg  Met  Leu  Tyr  Lys  Ala  Pro  Ser  Asp  Gly  Lys  Trp  Gly  Glu
               165                 170                      175

His  Glu  Val  Asp  Tyr  Leu  Leu  Phe  Ile  Val  Arg  Asp  Val  Lys  Leu  Gln
               180                 185                      190

Pro  Asn  Pro  Asp  Glu  Val  Ala  Glu  Ile  Lys  Tyr  Val  Ser  Arg  Glu  Glu
               195                 200                      205

Leu  Lys  Glu  Leu  Val  Lys  Lys  Ala  Asp  Ala  Gly  Asp  Glu  Ala  Val  Lys
          210                 215                 220

Leu  Ser  Pro  Trp  Phe  Arg  Leu  Val  Val  Asp  Asn  Phe  Leu  Met  Lys  Trp
     225                 230                 235                      240

Trp  Asp  His  Val  Glu  Lys  Gly  Thr  Ile  Thr  Glu  Ala  Ala  Asp  Met  Lys
               245                 250                      255

Thr  Ile  His  Lys  Leu
                260
```

( 2 ) INFORMATION FOR SEQ ID NO:19:

( i ) SEQUENCE CHARACTERISTICS:
        ( A ) LENGTH: 288 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Met  Thr  Ala  Asp  Asn  Asn  Ser  Met  Pro  His  Gly  Ala  Val  Ser  Ser  Tyr
1                   5                      10                       15

Ala  Lys  Leu  Val  Gln  Asn  Gln  Thr  Pro  Glu  Asp  Ile  Leu  Glu  Glu  Phe
               20                 25                      30

Pro  Glu  Ile  Ile  Pro  Leu  Gln  Gln  Arg  Pro  Asn  Thr  Arg  Ser  Ser  Glu
               35                 40                      45

Thr  Ser  Asn  Asp  Glu  Ser  Gly  Glu  Thr  Cys  Phe  Ser  Gly  His  Asp  Glu
     50                      55                      60

Glu  Gln  Ile  Lys  Leu  Met  Asn  Glu  Asn  Cys  Ile  Val  Leu  Asp  Trp  Asp
65                       70                 75                            80

Asp  Asn  Ala  Ile  Gly  Ala  Gly  Thr  Lys  Lys  Val  Cys  His  Leu  Met  Glu
               85                 90                       95

Asn  Ile  Glu  Lys  Gly  Leu  Leu  His  Arg  Ala  Phe  Ser  Val  Phe  Ile  Phe
               100                105                     110

Asn  Glu  Gln  Gly  Glu  Leu  Leu  Leu  Gln  Gln  Arg  Ala  Thr  Glu  Lys  Ile
               115                120                     125

Thr  Phe  Pro  Asp  Leu  Trp  Thr  Asn  Thr  Cys  Cys  Ser  His  Pro  Leu  Cys
     130                 135                 140

Ile  Asp  Asp  Glu  Leu  Gly  Leu  Lys  Gly  Lys  Leu  Asp  Asp  Lys  Ile  Lys
145                      150                 155                           160

Gly  Ala  Ile  Thr  Ala  Ala  Val  Arg  Lys  Leu  Asp  His  Glu  Leu  Gly  Ile
               165                 170                     175

Pro  Glu  Asp  Glu  Thr  Lys  Thr  Arg  Gly  Lys  Phe  His  Phe  Leu  Asn  Arg
               180                 185                     190

Ile  His  Tyr  Met  Ala  Pro  Ser  Asn  Glu  Pro  Trp  Gly  Glu  His  Glu  Ile
          195                 200                 205

Asp  Tyr  Ile  Leu  Phe  Tyr  Lys  Ile  Asn  Ala  Lys  Glu  Asn  Leu  Thr  Val
     210                 215                 220

Asn  Pro  Asn  Val  Asn  Glu  Val  Arg  Asp  Phe  Lys  Trp  Val  Ser  Pro  Asn
225                 230                 235                                240

Asp  Leu  Lys  Thr  Met  Phe  Ala  Asp  Pro  Ser  Tyr  Lys  Phe  Thr  Pro  Trp
```

|   |   |   |   |   | 245 |   |   |   |   | 250 |   |   |   |   | 255 |   |
|---|---|---|---|---|---|---|---|---|---|---|---|---|---|---|---|---|
| Phe | Lys | Ile | Ile | Cys | Glu | Asn | Tyr | Leu | Phe | Asn | Trp | Trp | Glu | Gln | Leu |
|   |   |   | 260 |   |   |   |   | 265 |   |   |   | 270 |   |   |   |
| Asp | Asp | Leu | Ser | Glu | Val | Glu | Asn | Asp | Arg | Gln | Ile | His | Arg | Met | Leu |
|   |   |   | 275 |   |   |   |   | 280 |   |   |   |   | 285 |   |   |

( 2 ) INFORMATION FOR SEQ ID NO:20:

( i ) SEQUENCE CHARACTERISTICS:
    ( A ) LENGTH: 456 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:20:

| Met | Asp | Thr | Leu | Leu | Lys | Thr | Pro | Asn | Leu | Glu | Phe | Leu | Pro | His | Gly |
|---|---|---|---|---|---|---|---|---|---|---|---|---|---|---|---|
| 1 |   |   |   | 5 |   |   |   |   | 10 |   |   |   |   | 15 |   |
| Phe | Val | Lys | Ser | Phe | Ser | Lys | Phe | Gly | Lys | Cys | Glu | Gly | Val | Cys | Val |
|   |   |   | 20 |   |   |   |   | 25 |   |   |   | 30 |   |   |   |
| Lys | Ser | Ser | Ala | Leu | Leu | Glu | Leu | Val | Pro | Glu | Thr | Lys | Lys | Glu | Asn |
|   |   | 35 |   |   |   |   | 40 |   |   |   |   | 45 |   |   |   |
| Leu | Asp | Phe | Glu | Leu | Pro | Met | Tyr | Asp | Pro | Ser | Lys | Gly | Val | Val | Asp |
|   | 50 |   |   |   |   | 55 |   |   |   |   | 60 |   |   |   |   |
| Leu | Ala | Val | Val | Gly | Gly | Pro | Ala | Gly | Leu | Ala | Val | Ala | Gln | Gln |
| 65 |   |   |   |   | 70 |   |   |   |   | 75 |   |   |   |   | 80 |
| Val | Ser | Glu | Ala | Gly | Leu | Ser | Val | Cys | Ser | Ile | Asp | Pro | Pro | Lys | Leu |
|   |   |   |   | 85 |   |   |   |   | 90 |   |   |   |   | 95 |   |
| Ile | Trp | Pro | Asn | Asn | Tyr | Gly | Val | Trp | Val | Asp | Glu | Phe | Glu | Ala | Met |
|   |   |   | 100 |   |   |   |   | 105 |   |   |   |   | 110 |   |   |
| Asp | Leu | Leu | Asp | Cys | Leu | Asp | Ala | Thr | Trp | Ser | Gly | Ala | Val | Tyr | Ile |
|   |   |   | 115 |   |   |   |   | 120 |   |   |   |   | 125 |   |   |
| Asp | Asp | Thr | Lys | Asp | Leu | Arg | Pro | Tyr | Gly | Arg | Val | Asn | Arg | Lys | Gln |
|   | 130 |   |   |   |   | 135 |   |   |   |   | 140 |   |   |   |   |
| Leu | Lys | Ser | Lys | Met | Met | Gln | Lys | Cys | Ile | Asn | Gly | Val | Lys | Phe | His |
| 145 |   |   |   |   | 150 |   |   |   |   | 155 |   |   |   |   | 160 |
| Gln | Ala | Lys | Val | Ile | Lys | Val | Ile | His | Glu | Glu | Lys | Ser | Met | Leu | Ile |
|   |   |   |   | 165 |   |   |   |   | 170 |   |   |   |   | 175 |   |
| Cys | Asn | Asp | Gly | Thr | Ile | Gln | Ala | Thr | Val | Val | Leu | Asp | Ala | Thr | Gly |
|   |   |   | 180 |   |   |   |   | 185 |   |   |   |   | 190 |   |   |
| Phe | Ser | Arg | Leu | Val | Gln | Tyr | Asp | Lys | Pro | Tyr | Asn | Pro | Gly | Tyr | Gln |
|   |   | 195 |   |   |   |   | 200 |   |   |   |   | 205 |   |   |   |
| Val | Ala | Tyr | Gly | Ile | Leu | Ala | Glu | Val | Glu | Glu | His | Pro | Phe | Asp | Lys |
|   | 210 |   |   |   |   | 215 |   |   |   |   | 220 |   |   |   |   |
| Met | Val | Phe | Met | Asp | Trp | Arg | Asp | Ser | His | Leu | Asn | Asn | Glu | Leu | Lys |
| 225 |   |   |   |   | 230 |   |   |   |   | 235 |   |   |   |   | 240 |
| Glu | Arg | Asn | Ser | Ile | Pro | Thr | Phe | Leu | Tyr | Ala | Met | Pro | Phe | Ser | Ser |
|   |   |   |   | 245 |   |   |   |   | 250 |   |   |   |   | 255 |   |
| Asn | Arg | Ile | Phe | Leu | Glu | Glu | Thr | Ser | Leu | Val | Ala | Arg | Pro | Gly | Leu |
|   |   |   | 260 |   |   |   |   | 265 |   |   |   |   | 270 |   |   |
| Arg | Met | Asp | Asp | Ile | Gln | Glu | Arg | Met | Val | Ala | Arg | Leu | His | Leu | Gly |
|   |   | 275 |   |   |   |   | 280 |   |   |   |   | 285 |   |   |   |
| Ile | Lys | Val | Lys | Ser | Ile | Glu | Glu | Asp | Glu | His | Cys | Val | Ile | Pro | Met |
|   | 290 |   |   |   |   | 295 |   |   |   |   | 300 |   |   |   |   |
| Gly | Gly | Pro | Leu | Pro | Val | Leu | Pro | Gln | Arg | Val | Val | Gly | Ile | Gly | Gly |
| 305 |   |   |   |   | 310 |   |   |   |   | 315 |   |   |   |   | 320 |

```
Thr  Ala  Gly  Met  Val  His  Pro  Ser  Thr  Gly  Tyr  Met  Val  Ala  Arg  Thr
                    325                      330                     335

Leu  Ala  Ala  Ala  Pro  Val  Ala  Asn  Ala  Ile  Ile  Tyr  Leu  Gly  Ser
               340            345                         350

Glu  Ser  Ser  Gly  Glu  Leu  Ser  Ala  Glu  Val  Trp  Lys  Asp  Leu  Trp  Pro
          355                      360                 365

Ile  Glu  Arg  Arg  Arg  Gln  Arg  Glu  Phe  Phe  Cys  Phe  Gly  Met  Asp  Ile
     370                 375                      380

Leu  Leu  Lys  Leu  Asp  Leu  Pro  Ala  Thr  Arg  Arg  Phe  Phe  Asp  Ala  Phe
385                      390                 395                           400

Phe  Asp  Leu  Glu  Pro  Arg  Tyr  Trp  His  Gly  Phe  Leu  Ser  Ser  Arg  Leu
                405                      410                      415

Phe  Leu  Pro  Glu  Leu  Ile  Val  Phe  Gly  Leu  Ser  Leu  Phe  Ser  His  Ala
               420                 425                      430

Ser  Asn  Thr  Ser  Arg  Glu  Ile  Met  Thr  Lys  Gly  Thr  Pro  Leu  Val  Met
          435                 440                      445

Ile  Asn  Asn  Leu  Leu  Gln  Asp  Glu
     450                 455
```

( 2 ) INFORMATION FOR SEQ ID NO:21:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Met  Glu  Cys  Val  Gly  Ala  Arg  Asn  Phe  Ala  Ala  Met  Ala  Val  Ser  Thr
1                   5                        10                      15

Phe  Pro  Ser  Trp  Ser  Cys  Arg  Arg  Lys  Phe  Pro  Val  Val  Lys  Arg  Tyr
               20                 25                      30

Ser  Tyr  Arg  Asn  Ile  Arg  Phe  Gly  Leu  Cys  Ser  Val  Arg  Ala  Ser  Gly
          35                      40                      45

Gly  Gly  Ser  Ser  Gly  Ser  Glu  Ser  Cys  Val  Ala  Val  Arg  Glu  Asp  Phe
     50                      55                      60

Ala  Asp  Glu  Glu  Asp  Phe  Val  Lys  Ala  Gly  Gly  Ser  Glu  Ile  Leu  Phe
65                  70                      75                           80

Val  Gln  Met  Gln  Gln  Asn  Lys  Asp  Met  Asp  Glu  Gln  Ser  Lys  Leu  Val
                85                      90                      95

Asp  Lys  Leu  Pro  Pro  Ile  Ser  Ile  Gly  Asp  Gly  Ala  Leu  Asp  His  Val
               100                 105                      110

Val  Ile  Gly  Cys  Gly  Pro  Ala  Gly  Leu  Ala  Leu  Ala  Ala  Glu  Ser  Ala
          115                      120                      125

Lys  Leu  Gly  Leu  Lys  Val  Gly  Leu  Ile  Gly  Pro  Asp  Leu  Pro  Phe  Thr
130                      135                      140

Asn  Asn  Tyr  Gly  Val  Trp  Glu  Asp  Glu  Phe  Asn  Asp  Leu  Gly  Leu  Gln
145                      150                      155                      160

Lys  Cys  Ile  Glu  His  Val  Trp  Arg  Glu  Thr  Ile  Val  Tyr  Leu  Asp  Asp
               165                      170                      175

Asp  Lys  Pro  Ile  Thr  Ile  Gly  Arg  Ala  Tyr  Gly  Arg  Val  Ser  Arg  Arg
               180                      185                      190

Leu  Leu  His  Glu  Glu  Leu  Leu  Arg  Arg  Cys  Val  Glu  Ser  Gly  Val  Ser
               195                      200                      205
```

| | | | | | | | | | | | | | | |
|---|---|---|---|---|---|---|---|---|---|---|---|---|---|---|
| Tyr | Leu 210 | Ser | Ser | Lys | Val | Asp 215 | Ser | Ile | Thr | Glu | Ala 220 | Ser | Asp | Gly | Leu |
| Arg 225 | Leu | Val | Ala | Cys | Asp 230 | Asp | Asn | Asn | Val | Ile 235 | Pro | Cys | Arg | Leu | Ala 240 |
| Thr | Val | Ala | Ser | Gly 245 | Ala | Ala | Ser | Gly | Lys 250 | Leu | Leu | Gln | Tyr | Glu 255 | Val |
| Gly | Gly | Pro | Arg 260 | Val | Cys | Val | Gln | Thr 265 | Ala | Tyr | Gly | Val | Glu 270 | Val | Glu |
| Val | Glu | Asn 275 | Ser | Pro | Tyr | Asp 280 | Pro | Asp | Gln | Met | Val | Phe 285 | Met | Asp | Tyr |
| Arg | Asp 290 | Tyr | Thr | Asn | Glu | Lys 295 | Val | Arg | Ser | Leu | Glu 300 | Ala | Glu | Tyr | Pro |
| Thr 305 | Phe | Leu | Tyr | Ala | Met 310 | Pro | Met | Thr | Lys | Ser 315 | Arg | Leu | Phe | Phe | Glu 320 |
| Glu | Thr | Cys | Leu | Ala 325 | Ser | Lys | Asp | Val | Met 330 | Pro | Phe | Asp | Leu | Leu 335 | Lys |
| Thr | Lys | Leu | Met 340 | Leu | Arg | Leu | Asp | Thr 345 | Leu | Gly | Ile | Arg | Ile 350 | Leu | Lys |
| Thr | Tyr | Glu 355 | Glu | Glu | Trp | Ser | Tyr 360 | Ile | Pro | Val | Gly | Gly 365 | Ser | Leu | Pro |
| Asn | Thr 370 | Glu | Gln | Lys | Asn | Leu 375 | Ala | Phe | Gly | Ala | Ala 380 | Ala | Ser | Met | Val |
| His 385 | Pro | Ala | Thr | Gly | Tyr 390 | Ser | Val | Val | Arg | Ser 395 | Leu | Ser | Glu | Ala | Pro 400 |
| Lys | Tyr | Ala | Ser | Val 405 | Ile | Ala | Glu | Ile | Leu 410 | Arg | Glu | Glu | Thr | Thr 415 | Lys |
| Gln | Ile | Asn | Ser 420 | Asn | Ile | Ser | Arg | Gln 425 | Ala | Trp | Asp | Thr | Leu 430 | Trp | Pro |
| Pro | Glu | Arg 435 | Lys | Arg | Gln | Arg | Ala 440 | Phe | Phe | Leu | Phe | Gly 445 | Leu | Ala | Leu |
| Ile | Val 450 | Gln | Phe | Asp | Thr | Glu 455 | Gly | Ile | Arg | Ser | Phe 460 | Phe | Arg | Thr | Phe |
| Phe 465 | Arg | Leu | Pro | Lys | Trp 470 | Met | Trp | Gln | Gly | Phe 475 | Leu | Gly | Ser | Thr | Leu 480 |
| Thr | Ser | Gly | Asp | Leu 485 | Val | Leu | Phe | Ala | Leu 490 | Tyr | Met | Phe | Val | Ile 495 | Ser |
| Pro | Asn | Asn | Leu 500 | Arg | Lys | Gly | Leu | Ile 505 | Asn | His | Leu | Ile | Ser 510 | Asp | Pro |
| Thr | Gly | Ala 515 | Thr | Met | Ile | Lys | Thr 520 | Tyr | Leu | Lys | Val | | | | |